United States Patent [19]

Kam Ming Chan et al.

[11] Patent Number: 4,594,465

[45] Date of Patent: Jun. 10, 1986

[54] COMPOUNDS CONTAINING A FLUOROBIPHENYLYL GROUP

[75] Inventors: Lawrence Kam Ming Chan, Hull; George W. Gray, Cottingham; Kenneth J. Toyne; David Lacey, both of Hull, all of England; Rudolf Eidensschink, Münster; Michael Römer, Rodgau, both of Fed. Rep. of Germany

[73] Assignees: The Secretary of State for Defence in Her Britannic Majesty's Government of the United Kingdom of Great Britain and Northern Ireland, London, England; Merck Patent Gesellschaft mit beschrankter Haftung, Fed. Rep. of Germany

[21] Appl. No.: 632,322

[22] Filed: Jul. 19, 1984

[30] Foreign Application Priority Data

Jul. 22, 1983 [GB] United Kingdom ............... 8319849

[51] Int. Cl.⁴ ............... C07C 43/20; C07C 25/18; C07C 69/017
[52] U.S. Cl. ............... 568/642; 570/129; 560/141; 568/643; 568/329; 252/299.66; 558/270
[58] Field of Search ............... 560/141; 568/642, 643, 568/329; 570/129; 260/463

[56] References Cited

U.S. PATENT DOCUMENTS

| | | | |
|---|---|---|---|
| 3,600,445 | 8/1971 | Wirth et al. | 568/643 X |
| 4,229,315 | 10/1980 | Krause et al. | 560/141 |
| 4,330,426 | 5/1982 | Eidenschink et al. | 568/642 X |
| 4,415,470 | 11/1983 | Eidenschink et al. | 568/642 X |
| 4,477,369 | 10/1984 | Sugimori et al. | 568/643 |
| 4,490,305 | 12/1984 | Eidenschink et al. | 568/642 |

FOREIGN PATENT DOCUMENTS 0064193 11/1982 European Pat. Off. ............ 568/642

*Primary Examiner*—Bernard Helfin
*Attorney, Agent, or Firm*—Stevens, Davis, Miller & Mosher

[57] ABSTRACT

Novel terphenyls having a relatively high clearing point and which are suitable for use in liquid crystal materials or in the preparation of compounds for use in such material are characterised by a formula:

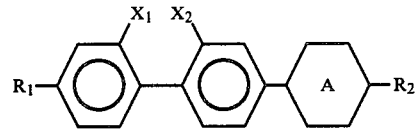

wherein:
$R_1$ is selected from H, alkyl, alkoxy, alkylcarbonyl, alkylcarbonyloxy and alkoxycarbonyloxy;
$R_2$ is selected from H, alkyl, alkoxy;
$X_1$ is selected from H and fluorine;
$X_2$ is selected from H and fluorine; and

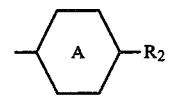

is selected from and (Abstract continued on next page.)

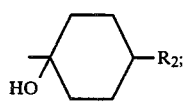
provided that one of X₁ and X₂ is fluroine. Compounds wherein
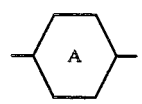
is
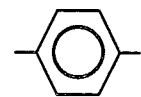
or
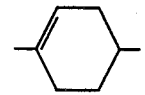
are generally useful as liquid crystal compounds.
5 Claims, 18 Drawing Figures

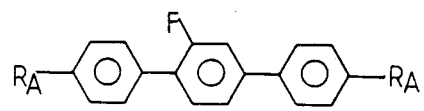 Ia
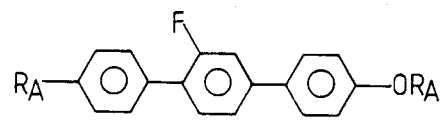 Ib
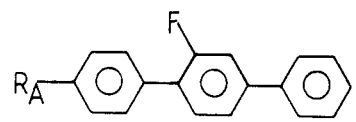 Ic
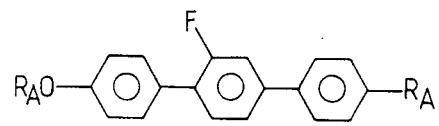 Id
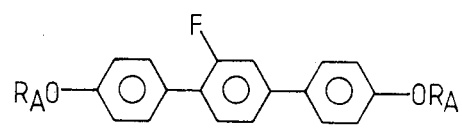 Ie
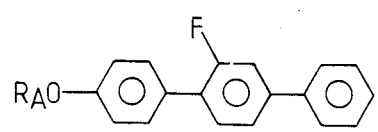 If
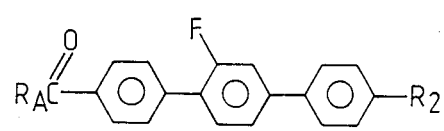 Ig
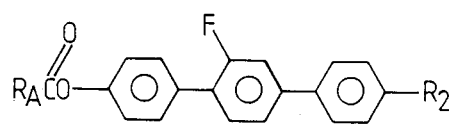 Ih
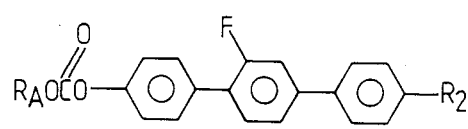 Ii
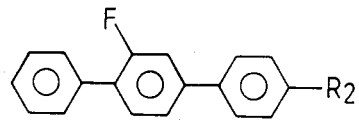 Ij
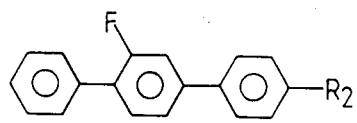 Ik
Fig.1.

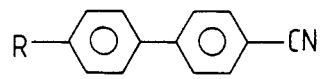 IIa
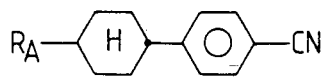 IIb
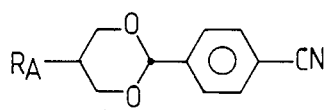 IIc
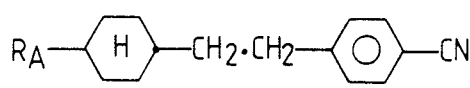 IId
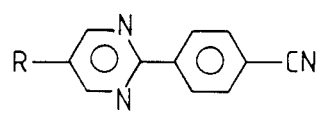 IIe
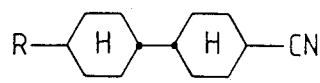 IIf
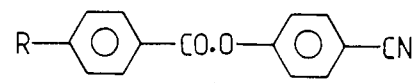 IIg
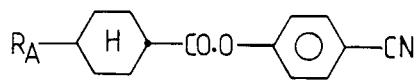 IIh
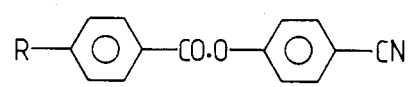 IIi
Fig. 8.

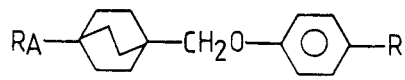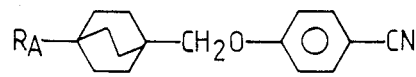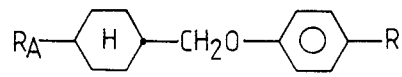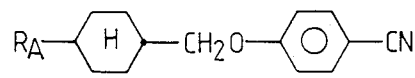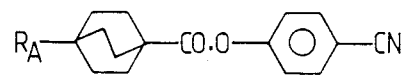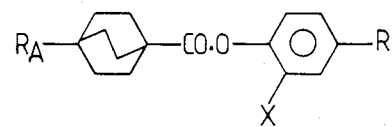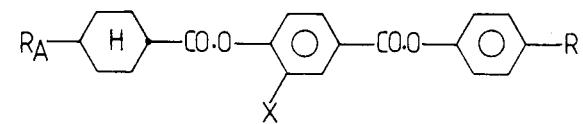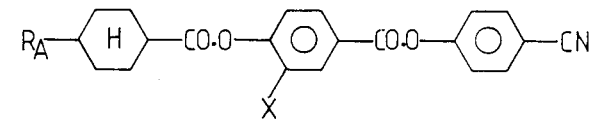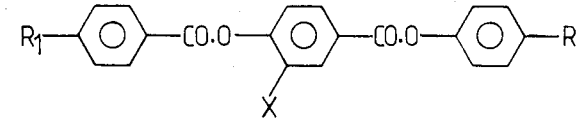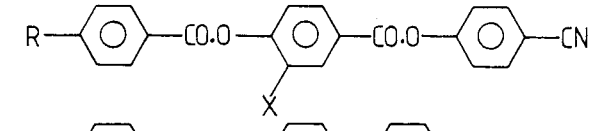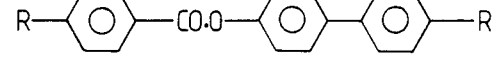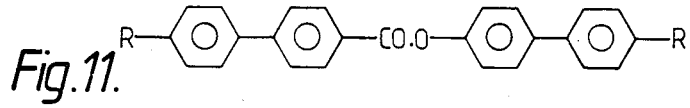
Fig.11.

COMPOUNDS CONTAINING A FLUOROBIPHENYLYL GROUP

The present invention relates to compounds containing a fluorobiphenylyl group and their use in and in the production of liquid crystal materials and devices.

The use of liquid crystal materials to exhibit electro-optical effects in display devices such as digital calculators, watches, meters and simple work displays is now well known. However, known liquid crystal materials are not ideal in all respects and a considerable amount of work is currently being carried out in the art to improve their properties.

Liquid crystal materials normally consist of specially selected mixture compositions and improved materials are obtained by forming new mixtures having an improved combination of properties.

The composition of a liquid crystal mixture for electro-optical applications depends on the kind of display effect to be utilised and the particular properties required for that effect. Examples of various display effects are given below. For all kinds however, it is desirable for the mixture to show the best possible combination of certain general properties, eg as follows:
  (i) a liquid crystalline temperature range—including room temperature (20° C.)—which is as wide as possible;
  (ii) a melting point (solid-to-liquid crystal transition temperature) which is as low as possible;
  (iii) a clearing point (liquid crystalline to isotropic liquid transition temperature) which is as high as possible;
  (iv) a positive or negative (as appropriate) dielectric anisotropy (permittivity measured parallel to the molecular axis less that measured perpendicular to the molecular axis) which is as great as possible in order to minimise the display voltage;
  (v) a viscosity which is as low as possible in order to minimise the display switching speeds;
  (vi) an electro-optical response which varies as little as possible with temperatures;
  (vii) a good chemical and photochemical stability;
Examples of further particular properties useful in specific applications are as follows:
  (viii) a good multiplexibility;
  (ix) an ability to switch dielectric anisotropy with frequency; and
  (x) a low birefringence;
  (xi) an ability to form by itself or in admixture with other compounds mainly nematic liquid crystalline phases, its tendency to form smectic liquid crystalline phases being kept to a minimum.

The required combination of properties of a liquid crystal mixture composition is obtained by blending together components or different properties in the mixture.

In order to keep production costs to a minimum it is desirable to use the smallest number of components in the mixture consistent with the achievement of a satisfactory combination of the required properties. Therefore it is desirable that the individual components used show a number of the required properties. It is desirable that the mutual solubility of the individual components is good, also in order to minimise the number of components.

The purpose of the present invention is to provide a class of novel compounds which provide suitable components for liquid crystal mixture compositions for electro-optical displays or are useful in the production of such compounds.

According to the present invention a first aspect there is provided a compound having a formula:

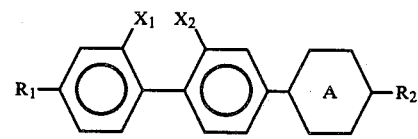

Formula I wherein:
  $R_1$ is selected from H, alkyl, alkoxy, alkylcarbonyl, alkylcarbonyloxy and alkoxycarbonyloxy;
  $R_2$ is selected from H, alkyl, alkoxy;
  $X_1$ is selected from H and fluorine;
  $X_2$ is selected from H and fluorine;
  and

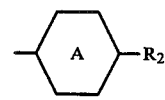

is selected from

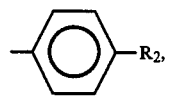

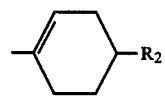

and

provided that one of $X_1$ and $X_2$ is fluorine. Compounds wherein

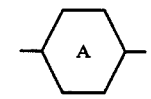

is

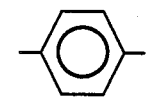

or

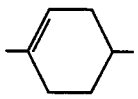

are generally useful as liquid crystal compounds. Compounds wherein

is

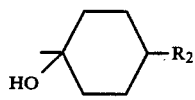

are generally useful in the preparation of the aforementioned fluoro-p-terphenyls although they may also show liquid crystal properties themselves.

By a 'liquid crystal' compound in this specification is meant a compound in one of the following two known categories:

(i) compounds which normally exhibit a liquid crystal phase;
(ii) compounds which do not normally exhibit a liquid crystal phase but which nevertheless usefully affect some aspect of liquid crystal behaviour when dissolved in other liquid crystal compounds.

Compounds in category (ii) show a 'monotropic' or a 'virtual' liquid crystal to isotropic liquid transition at a temperature below the melting point of their solid phase. The monotropic or virtual transition may be detected respectively by rapid cooling of the liquid phase or by dissolving the compound in a material exhibiting a liquid crystal phase, observing the change in the transition to the isotropic phase of the material by the addition and calculating the virtual transition temperature by extrapolation.

Compounds in category (ii) might for example be usefully dissolved in other liquid crystal compounds to extend or vary the liquid crystal temperature ranges of the compounds or to vary the molecular helical pitch (in the case of cholesteric liquid crystals).

In the accompanying drawings:

FIGS. 1 and 2 are lists of the generalised formulae of sub-classes of compound which are examples of the general class of Formula I;

FIGS. 8 to 11 are lists of the generalised formulae of known classes of compounds which may be mixed with compounds of Formula I to form liquid crystal mixtures;

Examples of sub-classes of compounds of Formula I wherein $X_1$ is H and $X_2$ is F are listed in FIG. 1 and the generalised formulae of these sub-classes are indicated by 'Ia' to 'Ik' respectively in FIG. 1. These compounds are referred to as '2'-fluoro' compounds of Formula I in this specification. In FIG. 1 each $R_A$ independently represents an alkyl group.

Figure 2:
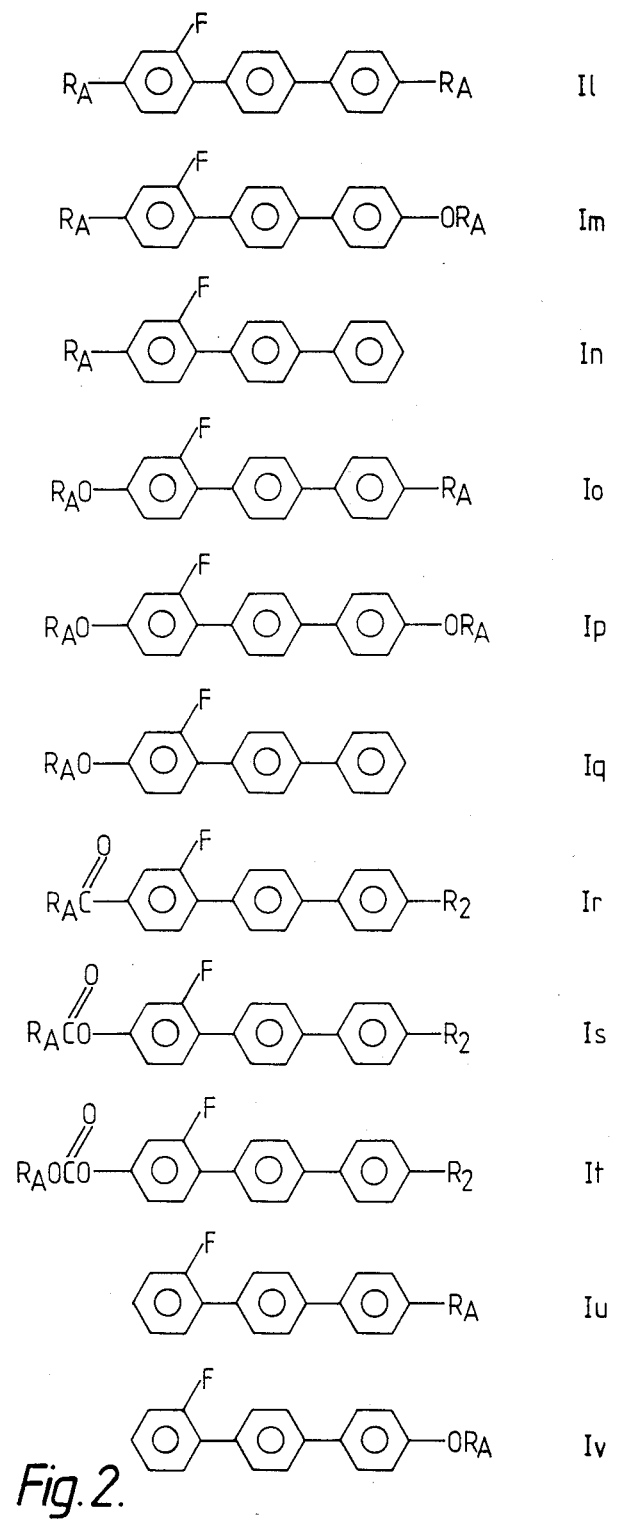

Examples of sub-classes of compounds of Formula I wherein $X_1$ is F and $X_2$ is H are listed in FIG. 2 and the generalised formulae of these sub-classes are indicated by 'Il' to 'Iv' respectively in FIG. 2. These compounds are referred to as '2-fluoro' compounds in this specification. Each $R_A$ independently represents an alkyl group in FIG. 2.

For use in nematic liquid crystal mixtures each group $R_A$ in any of the sub-classes listed in FIG. 1 or FIG. 2 is preferably an unbranched chain group. However, for use in chiral nematic (optically active) materials one or more groups $R_A$ contained in the molecule may independently be a chiral group, eg of the form $(+)-CH_3(CH_2)_nCH(CH_3)CH_2$, where n is from 1 to 8 and (+)-represents a chiral group having a positive optical rotation angle, eg (+)-2-methylbutyl.

Each alkyl group included in Formula I preferably has from 1 to 12, desirably 1 to 8 carbon atoms.

Thus in the sub-classes listed in FIGS. 1 and 2 each $R_A$ may be $C_{1-8}$ n-alkyl.

Preferred sub-classes are the di-alkyl terminated fluoro-p-terphenyls of Formulae Ia and Il wherein each $R_A$ independently represents a $C_{1-8}$ n-alkyl group.

The compounds of Formula I, particularly those of Formulae Ia and Il are very attractive components of liquid crystal materials for electro-optical display applications because they show:

(i) a relatively wide liquid crystalline temperature range;
(ii) a relatively high clearing point (liquid crystal-to-isotropic liquid transition temperature);
(iii) a relatively low melting point;
(iv) a reduced tendency to form smectic phases by themselves and in mixtures with other nematic materials;
(v) a relatively low viscosity by themselves and a reduced mixture viscosity when used in mixtures with nematic materials;
(vii) a reasonably low birefringence;
(viii) a good chemical and photochemical stability.

Compounds of Formula A as follows are known:

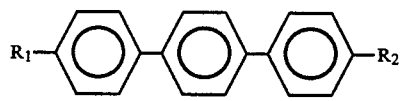

Formula A wherein $R_1$ and $R_2$ are for example alkyl groups. However, the fluorinated compounds of Formula I are more useful in practical devices than the corresponding compounds of Formula A because they can show:

(i) a much wider liquid crystalline temperature range;
(ii) a greater portion of the liquid crystalline phase which is nematic;
(iii) a reduced portion of the liquid crystalline phase which is smectic;
(iv) by themselves and especially in admixture with other nematic materials a depression of the temperature range at which any smectic phases are formed; as well as
(v) a lower melting point.

Examples of the comparison of specific properties of Formula I and Formula A compounds are given below (in Table 7).

According to one preferred feature of the invention a nematic or chiral nematic liquid crystal material comprises a mixture of two or more compounds of Formula I. Such a mixture may have a wide nematic or chiral nematic temperature range. The mixture may contain homologues of the same sub-class, eg 2 or more compounds of Formula Ia.

Alternatively, pairs of compounds may be formed having the same general structure but in different structural isomeric forms with regard to the groups $X_1$ and $X_2$. In other words one compound has $X_1 = F$ and $X_2 = H$ and the other has $X_2 = F$ and $X_1 = H$ in an otherwise identical structure (eg compounds of Formulae Ia and II). Such isomers have similar properties but a mixture of the two can give a very useful depression of melting point.

The compounds of Formula I may be used in applications other than electro-optical applications which are known to be suitable for the use of nematic or chiral nematic liquid crystal compounds. For example, the compounds of Formula I may be incorporated as high clearing point components of temperature senstive mixtures, eg thermochromic materials, eg for use in the applications described in UK Published Patent Application Nos. 2083244A and 2085585A.

Compounds of Formula I may be prepared by synthetic routes involving steps which are known per se, the overall route being new.

Figure 3:
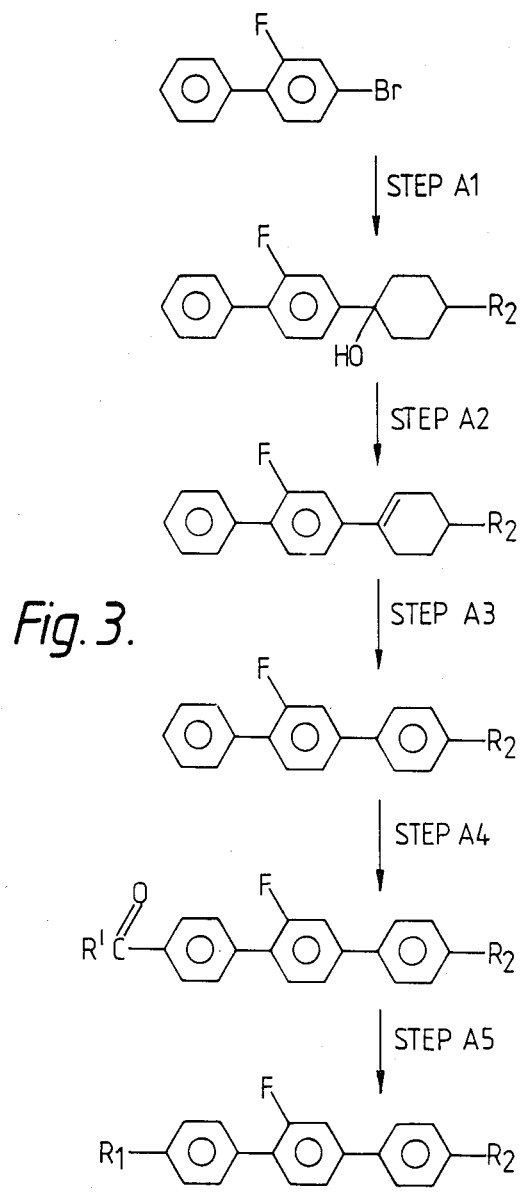
FIGS. 3 to 7 are flow diagrams respectively showing the preparation of various of the sub-classes listed in FIGS. 1 and 2.

For example, in FIG. 3 a generalised route, Route A is shown for the preparation of 2'-fluoro compounds of Formula I. In FIG. 3, $R_1$ = alkyl, preferably n-alkyl, and $R_2 = H$, alkyl, preferably n-alkyl or alkoxy preferably n-alkoxy. R' is $C_{m-1}H_{2m-1}$ where $R_1$ is $C_mH_{2m+1}$.

Figure 4:
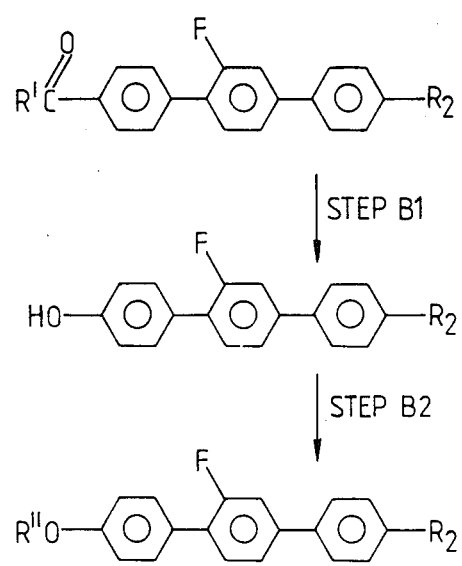

FIG. 4 shows a generalised route, Route B, for the preparation of 2'-fluoro compounds of Formula I wherein R'' is alkyl, alkylcarbonyl or alkoxycarbonyl. The starting material in Route B may be obtained from Route A (Steps A1 to A4) wherein $R' = CH_3$.

Figure 5:
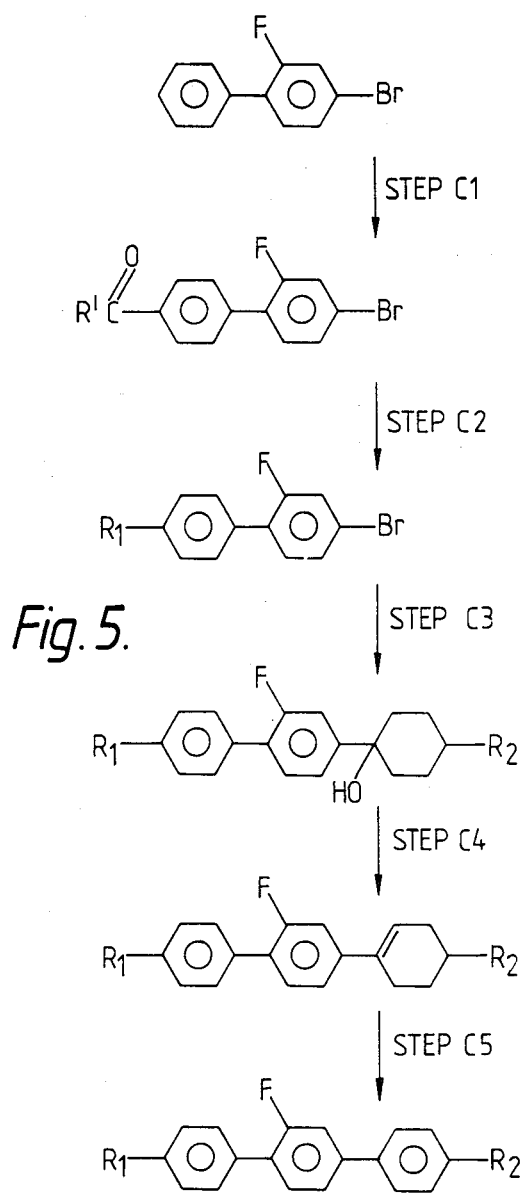

FIG. 5 shows a generalised route, Route C, for the preparation of 2'-fluoro compounds of Formula I wherein $R_1$ is alkyl, $C_mH_{2m+1}$, R' is alkyl $C_{m-1}$ and $R_2$ is H, alkoxy or alkyl.

Figure 6:
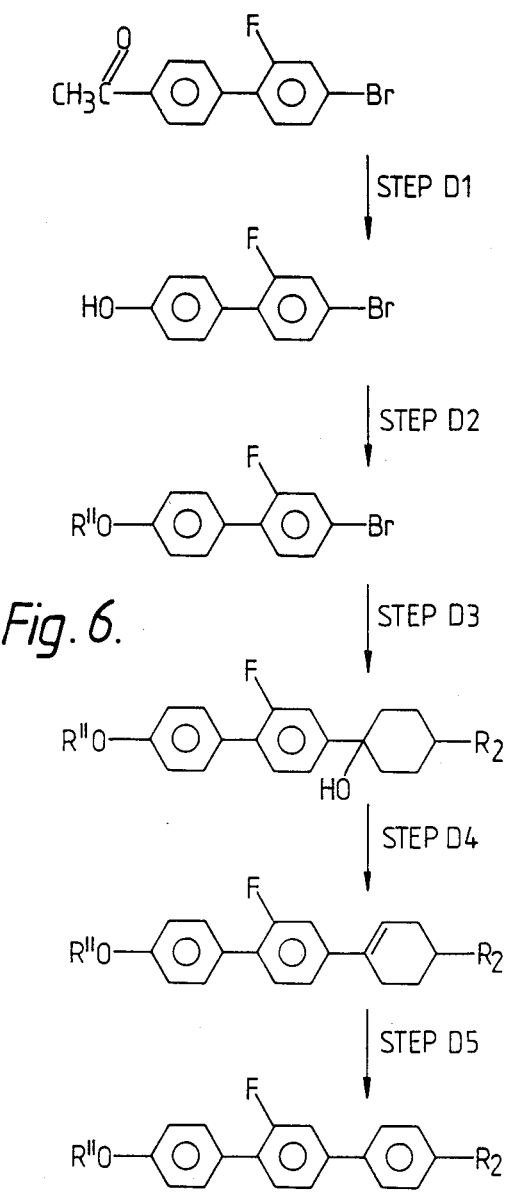

FIG. 6 shows a generalised route, Route D, for the preparation of 2'-fluoro compounds of Formula I wherein R'' is alkyl, alkylcarbonyl or alkoxycarbonyl.

2-Fluoro compounds of Formula I may be made by routes analogous to Routes A to D for the corresponding 2'-fluoro compounds.

Figure 7:
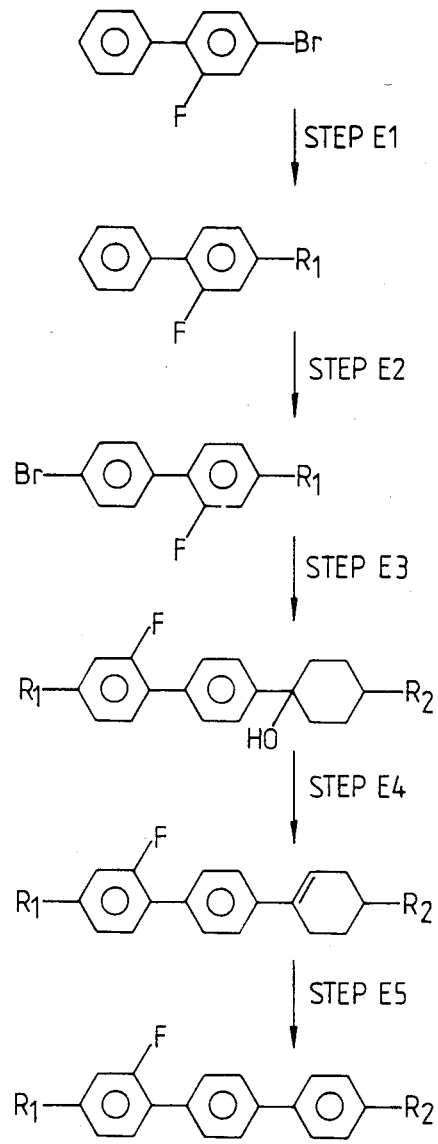

For example Route E (Steps E3 to E5) shown in FIG. 7 is analogous to Route C (Steps C3 to C5). In Route E $R_1$ = alkyl, preferably n-alkyl, and $R_2 = H$, alkyl, preferably n-alkyl, or alkoxy, preferably n-alkoxy. Steps E1 and E2 of Route E illustrate production of the appropriate starting material 2-fluoro-4-alkyl-4'-bromobiphenyl for Steps E3 to E5.

The compounds of Formula I have a relatively small negative dielectric anisotropy and may be added to liquid crystal materials of positive or negative dielectric anisotropy, known and referred to herein respectively as "positive" or "negative" materials in order to produce a mixture having amongst other things a suitable dielectric anisotropy. As is well known to those skilled in the art the dielectric anisotropy of the liquid crystal material is necessary for electro-optical operation and its sign (for a given frequency) is chosen according to the kind of electro-optical device in which the material is to be used.

Compounds of reasonably low melting point are preferred as positive high dielectric anisotropy components. For example, the compounds of the classes represented by the formulae listed in FIG. 8, labelled IIa to IIi respectively, are suitable as positive materials.

In FIG. 8 each R is independently n-alkyl or n-alkoxy and each $R_A$ is independently n-alkyl.

Alternatively, or additionally, the compounds of Formula I may be added to other small dielectric anisotropy compounds, eg to reduce mixture melting point, viscosity or to improve multiplexibility. The classes represented by the Formulae listed in FIG. 9 and labelled IIIa to IIIn are examples of such other compounds.

Figure 9:
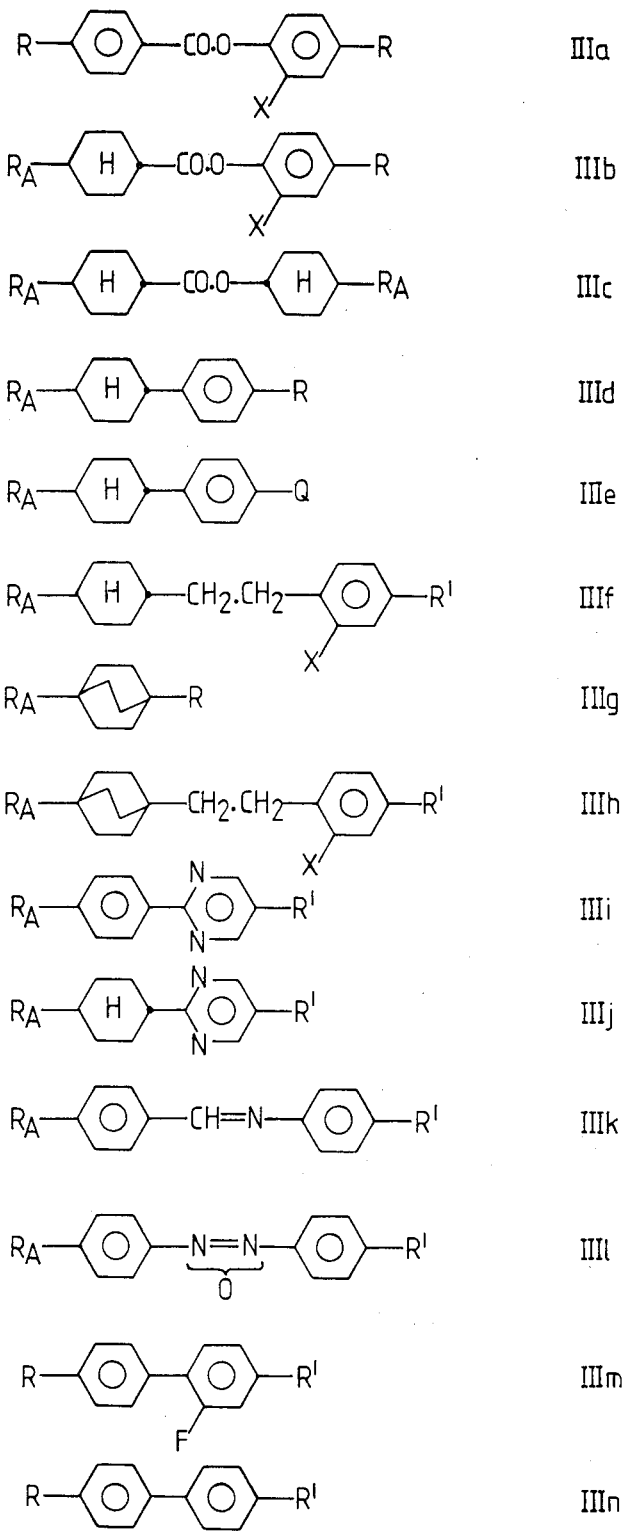

In FIG. 9
each R is independently n-alkyl or n-alkoxy
each $R_A$ is independently n-alkyl
each R' is independently n-alkyl, n-alkoxy or hydrogen;
X = H or F; and
Q = halogen, eg Cl or F.

Thus, one or more compounds of Formula I may be added to one or more compounds of Formula IIa to IIi listed in FIG. 8 optionally together with one or more compounds of Formula IIIa to IIIn listed in FIG. 9.

Figure 10:
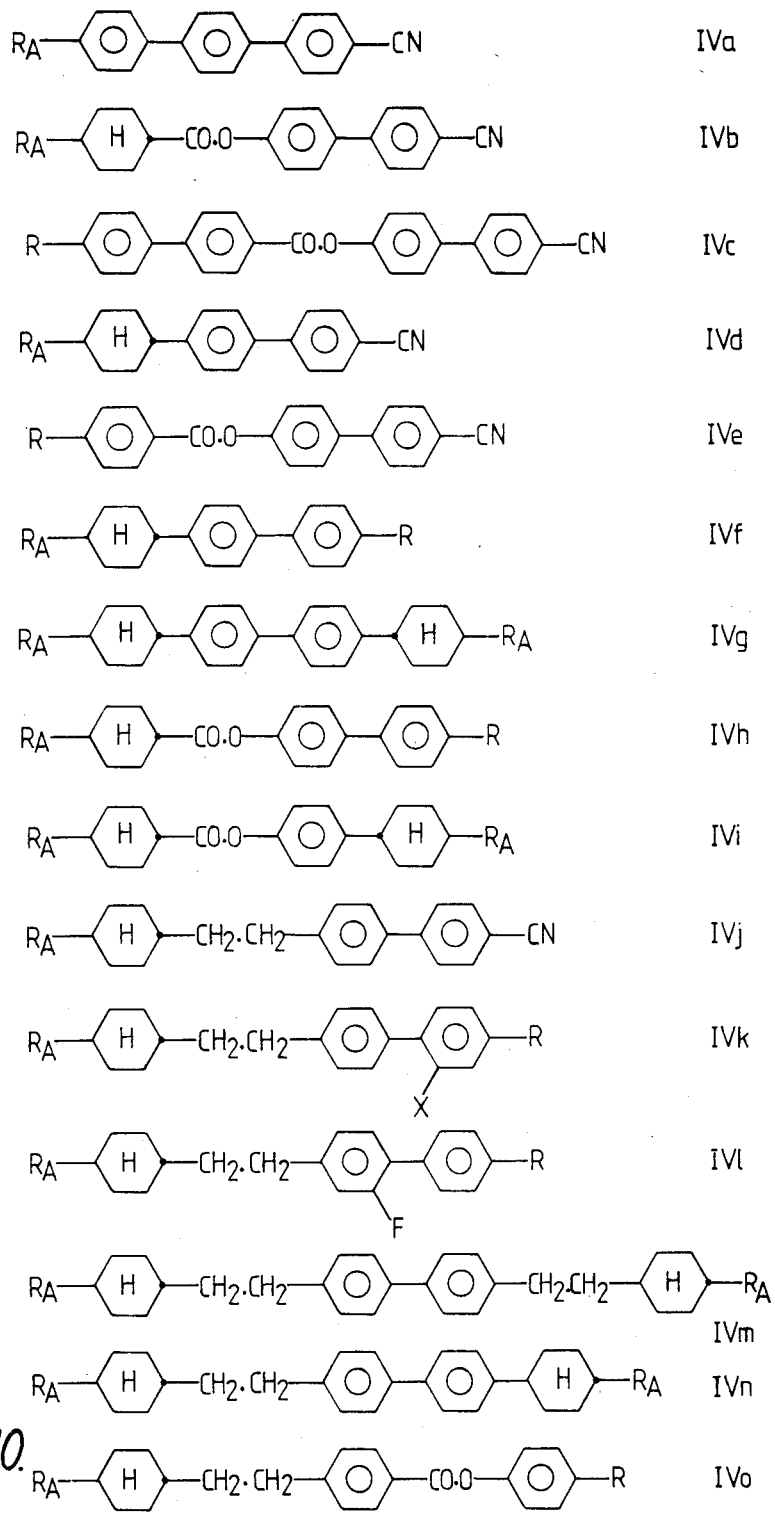

Additional high clearing point compounds may be included in such mixtures eg one or more compounds selected from the classes represented by the formulae listed in FIG. 10 labelled IVa to IV.

In FIG. 10 R, $R_A$ and X are as defined above for FIG. 9.

Other specific known additives, eg chiral additives, such as

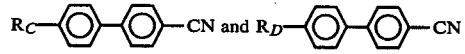

where $R_C = (+)$-2-methylbutyl and $R_D = (+)$-2-methylbutoxy, may be incorporated in the mixture where required.

The liquid crystal material obtained by blending together compounds of Formula I with those of the other classes as specified may be any one of the following:
(i) a positive nematic material for use in twisted nematic effect devices including multiplexed devices; an example of such a device is given below:
(ii) a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below:
(iii) a positive nematic material, preferably also with a pleochroic dye, for use in Fréedericksz effect devices (positive nematic type) in which the molecular arrangement may be changed from the homogeneous texture (OFF state) to the homeotropic texture (ON state) by an electric field:
(iv) a negative material which is a cholesteric (chiral nematic) of suitable resistivity (about $10^9$ ohm-cm), for use in cholesteric memory mode devices in which the molecular arrangement may be changed from a homogeneous texture (OFF state) to a scattering focal conic texture (ON state) by an electric field;

(v) a strongly negative material which is a cholesteric, preferably together also with a pleochroic dye, for use in cholesteric-to-nematic phase change effect devices (positive contrast type) in which the molecular arrangement may be changed from a weakly scattering, ie clear, surface aligned homeotropic texture (OFF state) to a strongly scattering twisted homogeneous texture (ON state) by an electric field:

(vi) a positive material which is a cholesteric, (chiral nematic) preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field:

(vii) a negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field:

(viii) a positive nematic material in two frequency switching effect devices (which may be twisted nematic effect devices) in which the dielectric anisotropy of the material may be changed in the ON state (at low frequency) from positive to negative by the application of a high frequency electric field:

(ix) a material suitable for the device described in copending UK Patent Application No. 8218821.

The construction and operation of the above devices and the general kinds of material which are suitable for use in them are themselves known.

Where a liquid crystal material is for use in a twisted nematic effect, cholesteric to nematic phase change effect (negative contrast type) or Fréedericksz effect (positive nematic type) device the material preferably contains:

Component A: one or more compounds of Formula I; plus

Component B: one or more compounds of Formula IIa to IIi optionally together with one or more of the following:

Component C: one or more compounds of Formula IIIa to IIIn;

Component D: one or more compounds of Formula IVa to IVo;

Component E: one or more chiral additives.

For the twisted nematic effect and Fréedericksz (positive nematic) effect the following percentages of the various components may be used in the material (the overall sum of the percentages adding to 100%).

Component A: 5 to 95% by weight (typically 5 to 40% by weight)

Component B: 5 to 60% by weight (typically 15% to 40% by weight)

Component C: 0 to 90% by weight (typically 5 to 30% by weight)

Component D: 0 to 40% by weight (typically 5 to 30% by weight)

Component E: 0 to 5% by weight (typically 0 to 1% by weight)

For the phase change (negative contrast type) the following proportions may be used:

Components A to D: in the percentages as specified above;

Component E: 2 to 20% (typically 4 to 5%) by weight.

For the Fréedericksz (positive nematic) and phase change (negative contrast type) effects a pleochroic dye forming from 1.5 to 15% of the overall mixture is preferably added to the liquid crystal material. Suitable dyes are described in published UK Patent Application Nos. 2081736A, 208219A and 2093475A. Typically, each dye compound incorporated forms 1 to 3% by weight of the overall mixture.

Liquid crystal mixtures including compounds of Formula I may be formed in a known way, eg simply by heating the constituent compounds together in the correct weight proportion to form an overall isotropic liquid (eg about 100° C.).

Examples of further generalised formulae of liquid crystal compounds which may be mixed with the components of the present invention are given in FIG. 11. Each R and $R_A$ is as defined above.

According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula I above.

The device according to the second aspect may be a twisted nematic effect device, which may or may not be operated in a multiplexed fashion, a cholesteric-to-nematic phase change effect device, a Fréedericksz effect device or a two-frequency switching effect device, all constructed in a known manner or any of the other devices mentioned above. The various ways in which compounds according to Formula I may be used in these devices are outlined above and will be further apparent to those skilled in the art.

Examples of the preparation and properties of compounds of Formula I embodying the present invention will now be given. In these Examples the following symbols are used:

C-I, mp=melting point
bp=boiling point
ir=infra-red spectroscopy
$^1$Hnmr=proton nuclear magnetic resonance
Rf=rate factor
ms=mass spectrometry
tlc=thin layer chromatogry
glc=gas liquid chromatography
hplc=high pressure liquid chromatography
g=grammes
h=hours
DSC=differential scanning calorimetry
Hg=mercury liquid crystal transition temperatures:
- C-N = crystal-to-nematic transition temperature
- C-S = crystal-to-smectic transition temperature
- S-S = smectic-to-smectic transition temperature
- S-I = smectic-to-isotropic transition temperature
- S-N = Smectic-to-nematic transition temperature
- N-I = nematic-to-isotropic transition temperature -continued S$_A$etc = smectic A phase, etc Brackets around a transition temperature eg (N-I) indicate a monotropic transition.

In the following Examples spectroscopic analysis (ir, $^1$H nmr and ms), tlc, glc and hplc were carried out on all the final products (and, where necessary, on the intermediates) to verify their structure and/or purity.

EXAMPLE 1

An example of Route A specified above wherein $R_1=n-C_5H_{11}$ and $R_2=n-C_3H_7$.

Step A1

As an example, the following procedure describes the preparation of cis-/trans-4-n-propyl-1-(2'-fluorobiphenyl-4'-yl)cyclohexanol.

About a third of a solution of 4-bromo-2-fluorobiphenyl (25.1 g, 0.10 mol) in sodium-dried ether (60 cm$^3$) was added to a flask containing magnesium turnings (2.40 g, 0.10 g atom). The reaction was initiated by the addition of a crystal of iodine and gentle warming. The remaining ethereal solution of 4-bromo-2-fluorobiphenyl was added dropwise so that the reaction mixture gently boiled. After the addition, the reaction mixture was gently heated under reflux for 1 hour. When the reaction mixture had cooled to room temperature, a solution of 4-n-propylcyclohexanone (0.10 mol) in sodium-dried ether (50 cm$^3$) was added over a period of ½-hour, and the resulting reaction mixture was then heated under reflux for a further ½-hour. The cooled solution was carefully poured onto a vigorously stirred mixture of concentrated sulphuric acid (25 cm$^3$) and crushed ice (300 g). The product was extracted into ether, and the combined ethereal extracts were washed with water and dried (MgSO$_4$). The crude residual alcohol was recrystallised from hexane.

From the results obtained from tlc and spectroscopic analyses (ir, $^1$Hnmr and ms), it was evident that the purified samples were isomeric mixtures, containing the cis- and trans-isomers in about equal amounts.

The pure cis- and trans-isomers of these compounds were isolated by column chromatography on silica gel, eluting with chloroform. The cis- and trans-isomers were recrystallised from hexane, but a positive identification as to which of the isomers was cis- and which trans- was not made.

The isomeric compounds prepared by Step A1 are given in Table 1 as follows:

TABLE 1

Isomeric compounds of formula:

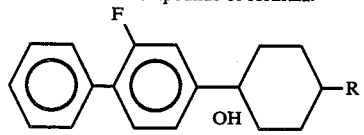

| R | R$_f$value | mp (°C.) | Yield |
|---|---|---|---|
| n-C$_3$H$_7$ | 0.45 | 89.5°, 96.5° (two crystal forms) | 65% |
| n-C$_3$H$_7$ | 0.55 | 69.0 | |

Step A2

The preparation of 4-n-propyl-1-(2'-fluorobiphenyl-4'-yl)cyclohexene.

A solution of the isomeric mixture of 4-n-propyl-1-(2'-fluorobiphenyl-4'-yl)cyclohexanols (0.06 mol) in sodium-dried benzene (100 cm$^3$) was added dropwise to a vigorously stirred mixture of phosphorus pentoxide (0.15 mol) in sodium-dried benzene (200 cm$^3$) over a period of ½-hour. The resulting reaction mixture was then stirred for 3 hours at room temperature. When cooled to 0° C., ice-water (300 cm$^3$) was added carefully. The aqueous phase was treated with benzene and the combined organic extracts were washed with 5% sodium carbonate solution and water, and then finally dried (MgSO$_4$). The crude residual cyclohexane was recrystallised from ethanol. A small sample of the pure material was obtained by column chromatography on silica gel, eluting with a 1:9 mixture of chloroform:petroleum ether (b p 60°-80° C.). The product was recrystallised from ethanol.

The product had the following properties: C-I=63.5° C., N-I=(57.2° C.).

Step A3

The preparation of 2-fluoro-4-n-propyl-p-terphenyl.

A solution of the 4-n-propyl-1-(2'-fluorobiphenyl-4'-yl)cyclohexene (0.05 mol), prepared as in Step A2, in sodium-dried toluene (100 cm$^3$) was added dropwise to a vigorously stirred mixture of 2,3-dichloro-5,6-dicyanobenzoquinone (0.11 mol) in sodium-dried toluene (200 cm$^3$) over a period of ½-hour. The reaction mixture was then heated under reflux at 110° C. for 3 hours. On cooling to room temperature, any precipitate of the quinol derived from quinone was filtered off, and the filtrate was washed with 15% sodium metabisulphite solution and with water. Finally, the solution in toluene was dried (MgSO$_4$).

The residual solid was sublimed (120°-140° C./0.01 mm Hg) and recrystallised from ethanol. This afforded 2-fluoro-4-n-propyl-p-terphenyl mp 74°-76° C. (72%) as a white crystalline solid.

Compounds of formula

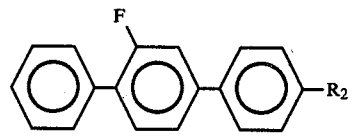

which may be prepared by a procedure analogous to Step A3 are those wherein R$_2$ is respectively: CH$_3$, CH$_3$O, C$_2$H$_5$, C$_2$H$_5$O, n-C$_3$H$_7$O, n-C$_4$H$_9$, C$_4$H$_9$O, n-C$_5$H$_{11}$, n-C$_5$H$_{11}$O, n-C$_6$H$_{13}$, n-C$_6$H$_{13}$O, n-C$_7$H$_{15}$, n$_7$H$_{15}$O, n-C$_8$H$_{17}$, n-C$_8$H$_{17}$O, n-C$_9$H$_{19}$, n-C$_9$H$_{19}$O, n-C$_{10}$H$_{21}$, n-C$_{10}$H$_{21}$O, n-C$_{11}$H$_{23}$, n-C$_{11}$H$_{23}$O, n-C$_{12}$H$_{25}$, n-C$_{12}$H$_{25}$O.

Step A4

The preparation of 2'-fluoro-4''-n-pentanoyl-4-n-propyl-p-terphenyl.

To a cooled stirred mixture of finely powdered anhydrous aluminium chloride (2.0 g, 0.015 mol) and 2'-fluoro-4-n-propyl-p-terphenyl (0.0125 mol) (prepared as in Step A3) in sieve-dried nitrobenzene (25 cm$^3$), a solution of pentanoyl chloride (0.015 mol) in sieve-dried nitrobenzene (5 cm$^3$) was added over a period of 15 minutes, the temperature being kept below 0° C. After stirring the reaction mixture at room temperature for 20 hours, it was poured onto a mixture of crushed ice (50 g), water (10 cm$^3$), and concentrated hydrochloric acid (10 cm³), and stirred vigorously for ½-hour. The aqueous phase was treated with chloroform and the combined organic extracts were washed with water. The chloroform and nitrobenzene were removed by steam distillation and the product was extracted into ether, the ethereal solution being washed with water prior to drying (MgSO₄). The resulting solid residue was purified by column chromatography on silica gel, eluting with a 2:1 mixture of chloroform/petroleum ether (bp 60°–80° C.) The product was recrystallised from 5% benzene/propan-2-ol (yield 66%).

Step A5

The preparation of 2'-fluoro-4''-n-pentyl-4-propyl-p-terphenyl.

The 2'-Fluoro-4''-n-pentanoyl-4-n-propyl-p-terphenyl (0.007 mol) prepared in Step A4 was added to a stirred mixture of diethylene glycol (50 cm³), hydrazine hydrate (0.035 mol), and potassium hydroxide (0.0175 mol), and the reaction mixture was heated at 130° C. for 2 hours. The excess of hydrazine was distilled off and the temperature of the reaction mixture was raised to 180° C. for 4 hours. On cooling to room temperature, the reaction mixture was poured into water (1000 cm³), and the product was extracted into ether. The combined ethereal extracts were then washed with water and dried (MgSO₄). The pale yellow residue was purified by column chromatography on silica gel, eluting with a 1:5 mixture of chloroform/petroleum ether (bp 60°–80° Recrystallisation from propan-2-ol afforded the product as a white crystalline solid.

The product, 2'-fluoro-4''-n-pentyl-4-n-propyl-p-terphenyl had the following properties: C-N=50° C.; N-I=140.6° C. The yield was 38%.

Examples of products prepared by a procedure analogous to Example 1 are given in Table 2 as follows.

TABLE 2

Compounds of formula:

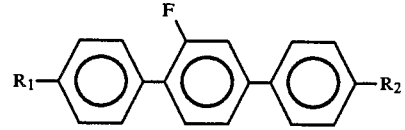

| $R_1$ | $R_2$ | $R_1$ | $R_2$ | $R_1$ | $R_2$ |
|---|---|---|---|---|---|
| CH₃ | CH₃ | C₂H₅ | CH₃ | n-C₃H₇ | CH₃ |
| CH₃ | C₂H₅ | C₂H₅ | C₂H₅ | n-C₃H₇ | C₂H₅ |
| CH₃ | n-C₃H₇ | C₂H₅ | n-C₃H₇ | n-C₃H₇ | n-C₃H₇ |
| CH₃ | n-C₄H₉ | C₂H₅ | n-C₄H₉ | n-C₃H₇ | n-C₄H₉ |
| CH₃ | n-C₅H₁₁ | C₂H₅ | n-C₅H₁₁ | n-C₃H₇ | n-C₅H₁₁ |
| CH₃ | n-C₆H₁₃ | C₂H₅ | n-C₆H₁₃ | n-C₃H₇ | n-C₆H₁₃ |
| CH₃ | n-C₇H₁₅ | C₂H₅ | n-C₇H₁₅ | n-C₃H₇ | n-C₇H₁₅ |
| CH₃ | H | C₂H₅ | H | n-C₃H₇ | H |
| CH₃ | CH₃O | C₂H₅ | CH₃O | n-C₃H₇ | CH₃O |
| CH₃ | C₂H₅O | C₂H₅ | C₂H₅O | n-C₃H₇ | C₂H₅O |
| CH₃ | n-C₃H₇O | C₂H₅ | n-C₃H₇O | n-C₃H₇ | n-C₃H₇O |
| CH₃ | n-C₄H₉O | C₂H₅ | n-C₄H₉O | n-C₃H₇ | n-C₄H₉O |
| CH₃ | n-C₅H₁₁O | C₂H₅ | n-C₅H₁₁O | n-C₃H₇ | n-C₅H₁₁O |
| CH₃ | n-C₆H₁₃O | C₂H₅ | n-C₆H₁₃O | n-C₃H₇ | n-C₆H₁₃O |
| CH₃ | n-C₇H₁₅O | C₂H₅ | n-C₇H₁₅O | n-C₃H₇ | n-C₇H₁₅O |
| CH₃ | n-C₈H₁₇ | C₂H₅ | n-C₈H₁₇ | n-C₃H₇ | n-C₈H₁₇ |
| CH₃ | n-C₈H₁₇O | C₂H₅ | n-C₈H₁₇O | n-C₃H₇ | n-C₈H₁₇O |
| CH₃ | n-C₉H₁₉ | C₂H₅ | n-C₉H₁₉ | n-C₃H₇ | n-C₉H₁₉ |
| CH₃ | n-C₉H₁₉O | C₂H₅ | n-C₉H₁₉O | n-C₃H₇ | n-C₉H₁₉O |
| CH₃ | n-C₁₀H₂₁ | C₂H₅ | n-C₁₀H₂₁ | n-C₃H₇ | n-C₁₀H₂₁ |
| CH₃ | n-C₁₀H₂₁O | C₂H₅ | n-C₁₀H₁₂O | n-C₃H₇ | n-C₁₀H₂₁O |
| CH₃ | n-C₁₁H₂₃ | C₂H₅ | n-C₁₁H₂₃ | n-C₃H₇ | n-C₁₁H₂₃ |
| CH₃ | n-C₁₂H₂₅ | C₂H₅ | n-C₁₂H₂₅ | n-C₃H₇ | n-C₁₂H₂₅ |

| $R_1$ | $R_2$ | $R_4$ | $R_2$ | $R_1$ | $R_2$ |
|---|---|---|---|---|---|
| n-C₄H₉ | CH₃ | n-C₅H₁₁ | CH₃ | n-C₆H₁₃ | CH₃ |
| n-C₄H₉ | C₂H₅ | n-C₅H₁₁ | C₂H₅ | n-C₆H₁₃ | C₂H₅ |
| n-C₄H₉ | n-C₃H₇ | n-C₅H₁₁ | n-C₃H₇ | n-C₆H₁₃ | n-C₃H₇ |
| n-C₄H₉ | n-C₄H₉ | n-C₅H₁₁ | n-C₄H₉ | n-C₆H₁₃ | n-C₄H₉ |
| n-C₄H₉ | n-C₅H₁₁ | n-C₅H₁₁ | n-C₅H₁₁ | n-C₆H₁₃ | n-C₅H₁₁ |
| n-C₄H₉ | n-C₆H₁₃ | n-C₅H₁₁ | n-C₆H₁₃ | n-C₆H₁₃ | n-C₆H₁₃ |
| n-C₄H₉ | n-C₇H₁₅ | n-C₅H₁₁ | n-C₇H₁₅ | n-C₆H₁₃ | n-C₇H₁₅ |
| n-C₄H₉ | H | n-C₅H₁₁ | H | n-C₆H₁₃ | H |
| n-C₄H₉ | CH₃O | n-C₅H₁₁ | CH₃O | n-C₆H₁₃ | CH₃O |
| n-C₄H₉ | C₂H₅O | n-C₅H₁₁ | C₂H₅O | n-C₆H₁₃ | C₂H₅O |
| n-C₄H₉ | n-C₃H₇O | n-C₅H₁₁ | n-C₃H₇O | n-C₆H₁₃ | n-C₃H₇O |
| n-C₄H₉ | n-C₄H₉O | n-C₅H₁₁ | n-C₄H₉O | n-C₆H₁₃ | n-C₄H₉O |
| n-C₄H₉ | n-C₅H₁₁O | n-C₅H₁₁ | n-C₅H₁₁O | n-C₆H₁₃ | n-C₅H₁₁O |
| n-C₄H₉ | n-C₆H₁₃O | n-C₅H₁₁ | n-C₆H₁₃O | n-C₆H₁₃ | n-C₆H₁₃O |
| n-C₄H₉ | n-C₇H₁₅O | n-C₅H₁₁ | n-C₇H₁₅O | n-C₆H₁₃ | n-C₇H₁₅O |
| n-C₄H₉ | n-C₈H₁₇ | n-C₅H₁₁ | n-C₈H₁₇ | n-C₆H₁₃ | n-C₈H₁₇ |
| n-C₄H₉ | n-C₈H₁₇O | n-C₅H₁₁ | n-C₈H₁₇O | n-C₆H₁₃ | n-C₈H₁₇O |
| n-C₄H₉ | n-C₉H₁₉ | n-C₅H₁₁ | n-C₉H₁₉ | n-C₆H₁₃ | n-C₉H₁₉ |
| n-C₄H₉ | n-C₉H₁₉O | n-C₅H₁₁ | n-C₉H₁₉O | n-C₆H₁₃ | n-C₉H₁₉O |
| n-C₄H₉ | n-C₁₀H₂₁ | n-C₅H₁₁ | n-C₁₀H₂₁ | n-C₆H₁₃ | n-C₁₀H₂₁ |
| n-C₄H₉ | n-C₁₀H₂₁O | n-C₅H₁₁ | n-C₁₀H₂₁O | n-C₆H₁₃ | n-C₁₀H₂₁O |
| n-C₄H₉ | n-C₁₁H₂₃ | n-C₅H₁₁ | n-C₁₁H₂₃ | n-C₆H₁₃ | n-C₁₁H₂₃ |
| n-C₄H₉ | n-C₁₂H₂₅ | n-C₅H₁₁ | n-C₁₂H₂₅ | n-C₆H₁₃ | n-C₁₂H₂₅ |
| n-C₄H₉ | n-C₁₂H₂₅O | n-C₅H₁₁ | n-C₁₂H₂₅O | n-C₆H₁₃ | n-C₁₂H₂₅O |

| $R_1$ | $R_2$ | $R_1$ | $R_2$ | $R_1$ | $R_2$ |
|---|---|---|---|---|---|

TABLE 2-continued

Compounds of formula:

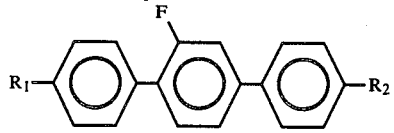

| | | | | | |
|---|---|---|---|---|---|
| n-C7H15 | CH3 | n-C8H17 | CH3 | n-C9H19 | CH3 |
| n-C7H15 | C2H5 | n-C8H17 | C2H5 | n-C9H19 | C2H5 |
| n-C7H15 | n-C3H7 | n-C8H17 | n-C3H7 | n-C9H19 | n-C3H7 |
| n-C7H15 | n-C4H9 | n-C8H17 | n-C4H9 | n-C9H19 | n-C4H9 |
| n-C7H15 | n-C5H11 | n-C8H17 | n-C5H11 | n-C9H19 | n-C5H11 |
| n-C7H15 | n-C6H13 | n-C8H17 | n-C6H13 | n-C9H19 | n-C6H13 |
| n-C7H15 | n-C7H15 | n-C8H17 | n-C7H15 | n-C9H19 | n-C7H15 |
| n-C7H15 | H | n-C8H17 | n-C8H17 | n-C9H19 | n-C8H17 |
| n-C7H15 | CH3O | n-C8H17 | CH3O | n-C9H19 | H |
| n-C7H15 | C2H5O | n-C8H17 | C2H5O | n-C9H19 | CH3O |
| n-C7H15 | n-C3H7O | n-C8H17 | n-C3H7O | n-C9H19 | C2H5O |
| n-C7H15 | n-C4H9O | n-C8H17 | n-C4H9O | n-C9H19 | n-C3H7O |
| n-C7H15 | n-C5H11O | n-C8H17 | n-C5H11O | n-C9H19 | n-C4H9O |
| n-C7H15 | n-C6H13O | n-C8H17 | n-C6H13O | n-C9H19 | n-C5H11O |
| n-C7H15 | n-C7H15O | n-C8H17 | n-C7H15O | n-C9H19 | n-C6H13O |
| n-C7H15 | n-C8H17 | n-C8H17 | n-C8H17O | n-C9H19 | n-C7H15O |
| n-C7H15 | n-C8H17O | n-C8H17 | n-C9H19 | n-C9H19 | n-C8H17O |
| n-C7H15 | n-C9H19 | n-C8H17 | n-C9H19O | n-C9H19 | n-C9H19 |
| n-C7H15 | n-C9H19O | n-C8H17 | n-C10H21 | n-C9H19 | n-C9H19O |
| n-C7H15 | n-C10H21 | n-C8H17 | n-C10H21O | n-C9H19 | n-C10H21 |
| n-C7H15 | n-C10H21O | n-C8H17 | n-C11H23 | n-C9H19 | n-C10H21O |
| n-C7H15 | n-C11H23 | n-C8H17 | n-C12H25 | n-C9H19 | n-C11H23 |
| n-C7H15 | n-C12H25 | n-C8H17 | n-C12H25O | n-C9H19 | n-C12H25O |
| n-C7H15 | n-C12H25O | | | | |
| n-C10H21 | CH3 | n-C11H23 | CH3 | n-C12H25 | CH3 |
| n-C10H21 | C2H5 | n-C11H23 | C2H5 | n-C12H25 | C2H5 |
| n-C10H21 | n-C3H7 | n-C11H23 | n-C3H7 | n-C12H25 | n-C3H7 |
| n-C10H21 | n-C4H9 | n-C11H23 | n-G4H9 | n-C12H25 | n-C4H9 |
| n-C10H21 | n-C5H11 | n-C11H23 | n-C5H11 | n-C12H25 | n-C5H11 |
| n-C10H21 | n-C6H13 | n-C11H23 | n-C6H13 | n-C12H25 | n-C6H13 |
| n-C10H21 | n-C7H15 | n-C11H23 | n-C7H15 | n-C12H25 | n-C7H15 |
| n-C10H21 | n-C8H17 | n-C11H23 | n-C8H17 | n-C12H25 | n-C8H17 |
| n-C10H21 | n-C9H19 | n-C11H23 | n-C9H19 | n-C12H25 | n-C9H19 |
| n-C10H21 | n-C10H21 | n-C11H23 | n-C10H21 | n-C12H25 | n-C10H21 |
| n-C10H21 | n-C11H23 | n-C11H23 | n-C11H23 | n-C12H25 | n-C11H23 |
| n-C10H21 | n-C12H25 | n-C11H23 | n-C12H25 | n-C12H25 | n-C12H25 |
| n-C10H21 | H | n-C11H23 | H | n-C12H25 | H |
| n-C10H21 | CH3O | n-C11H23 | CH3O | n-C12H25 | CH3O |
| n-C10H21 | C2H5O | n-C11H23 | C2H5O | n-C12H25 | C2H5O |
| n-C10H21 | n-C3H7O | n-C11H23 | n-C3H7O | n-C12H25 | n-C3H7O |
| n-C10H21 | n-C4H9O | n-C11H23 | n-C4H90 | n-C12H25 | n-C4H9O |
| n-C10H21 | n-C5H11O | n-C11H23 | n-C5H11O | n-C12H25 | n-C5H11O |
| n-C10H21 | n-C6H13O | n-C11H23 | n-C6H13O | n-C12H25 | n-C6H13O |
| n-C10H21 | n-C7H15O | n-C11H23 | n-C7H15O | n-C12H25 | n-C7H15O |
| n-C10H21 | n-C8H17O | n-C11H23 | n-C8H17O | n-C12H25 | n-C8H17O |
| n-C10H21 | n-C9H19O | n-C11H23 | n-C19H19O | n-C12H25 | n-C9H19O |
| n-C10H21 | n-C10H21O | n-C11H23 | n-C10H21O | n-C12H25 | n-C10H21O |
| n-C10H21 | n-C12H25O | n-C12H23 | n-C12H25O | n-C12H25 | n-C12H25O |

As examples of properties of the compounds listed in Table 2 where $R_1=C_2H_5$ and $R_2=n-C_5H_{11}$ the compound has the properties C-S=64.0° C.; S-N=90° C.; N-I=128.7° C.; where $R_1=n-C_3H_7$ and $R_2=n-C_5H_{11}$ the compound* has the properties C-S=61.0° C.; S-N=99.5° C. and N-I=141.5° C. and where $R_1=n-C_4H_9$ and $R_2=n-C_5H_{11}$ the compound has the properties C-S=68° C.; S-N=106.8° C. and N-I=131.2° C.

* This compound has also showed a crystal-crystal transition at 50° C., measured by DSC.

The clearing transition temperatures of various examples of compounds of formula

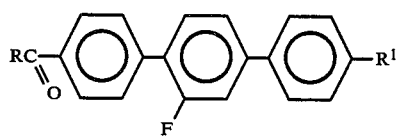

are as given in Table 3a as follows:

TABLE 3a

| R | $R^1$ | mp (°C.) | S-I | N-I |
|---|---|---|---|---|
| C2H5 | n-C3H7 | 90.5° | | 214.5° |
| n-C3H7 | n-C3H7 | 94.5° | | 185.0 |
| n-C5H11 | n-C3H7 | 91.0° | 189.0° | |
| n-C6H13 | n-C3H7 | 84.0° | 188.0° | |
| n-C7H15 | n-C3H7 | 95.0° | 186.0° | |
| n-C8H17 | n-C3H7 | 91.5° | 183.5° | |
| C2H5 | n-C5H11 | 56.0° | | 208.0° |
| n-C3H7 | n-C5H11 | 70.5° | 185.5° | |
| n-C4H9 | n-C5H11 | 81.0° | 192.2° | |

The main transition temperatures of various compounds of Formula

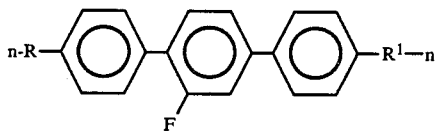

are given in Table 3b as follows:

TABLE 3b

| Compound Number | R | $R^1$ | mp (°C.) | N-I (°C.) |
|---|---|---|---|---|
| 1 | H | $C_3H_7$ | 75.5 | |
| 2 | $C_2H_5$ | $CH_3$ | 115.0 | 138.2 |
| 3 | $C_3H_7$ | H | 95.0 | |
| 4 | $C_3H_7$ | $CH_3$ | 114.0 | 150.5 |
| 5 | $C_3H_7$ | $C_2H_5$ | 73.5 | 133.3 |
| 6 | $C_2H_5$ | $C_3H_7$ | 78.0 | 133.0 |
| 7 | $C_3H_7$ | $C_3H_7$ | 88.0 | 145.7 |
| 8 | $C_4H_9$ | $C_3H_7$ | 56.5 | 133.5 |
| 9 | $C_5H_{11}$ | $C_3H_7$ | 50.0 | 140.6 |
| 10 | $C_6H_{13}$ | $C_3H_7$ | 44.5 | 132.0 |
| 11 | $C_7H_{15}$ | $C_3H_7$ | 40.5 | 133.5 |
| 12 | $C_8H_{17}$ | $C_3H_7$ | 49.0 | 127.0 |
| 13 | $C_9H_{19}$ | $C_3H_7$ | 46.0 | 126.5 |
| 14 | $C_{10}H_{21}$ | $C_3H_7$ | 58.0 | 121.7 |
| 15 | $C_{11}H_{23}$ | $C_3H_7$ | 54.5 | 120.6 |
| 16 | $C_5H_{11}$ | H | 71.0 | (47.0) |
| 17 | $CH_3$ | $C_5H_{11}$ | 83.0 | |
| 18 | $C_2H_5$ | $C_5H_{11}$ | 64.0 | 128.7 |
| 19 | $C_3H_7$ | $C_5H_{11}$ | 61.0 | 141.5 |
| 20 | $C_4H_9$ | $C_5H_{11}$ | 68.0 | 131.2 |
| 21 | $C_5H_{11}$ | $C_5H_{11}$ | 51.5 | 136.5 |

Additional transition temperatures shown by compounds listed in Table 3b are given in Table 3c as follows:

TABLE 3b

| Compound Number | Transition Temperature | | | | | |
|---|---|---|---|---|---|---|
| | $S_{K,J}-S_X$ | $S_X-S_C$ | $S_B-S_A$ | $S_C-S_A$ | $S_C-N$ | $S_A-N$ |
| 8 | | | | | | (52.5) |
| 10 | | (37.5) | | (42.0) | | |
| 11 | (18.8) | (29.5) | | | 42.5 | |
| 12 | | (39.2) | | (40.5) | | 86.8 |
| 13 | | (35.0) | | 52.2 | | 89.0 |
| 14 | | | (40.5) | | | 95.5 |
| 15 | | | (42.5) | | | 97.2 |
| 18 | | | | | | 90.0 |
| 19 | | | | | | 99.5 |
| 20 | | | | | | 106.8 |
| 21 | | | 62.0 | | | 109.5 |

EXAMPLE 2

An example of Route B specified above wherein $R_1=C_4H_9O$ and $R_2=n-C_3H_7$.

Step B1

The methyl p-terphenylylketone ($R^1=CH_3$, $R_2=n-C_3H_7$) produced by the procedure of Step A4 of Route A was converted into the corresponding hydroxy compound using 1.25 equivalents m-chloroperoxybenzoic acid in dry dichloromethane (Baeyer-Villiger Oxidation); the resulting ester was hydrolysed to the appropriate phenol with 10% ethanolic potassium hydroxide.

Step B2

The resulting hydroxy compound produced by Step B1 was alkylated ($R_1=n-C_5H_{11}$) using a standard method from the literature, eg as described in J. Chem. Soc., P1467 (1954) by G. W. Gray and B. Jones.

Analogous compounds with the 4-substituent being either alkoxy (OR) or hydrogen (H) which may be prepared by an analogous procedure are listed in Table 3 as follows.

TABLE 3

Compounds of formula

| $R_1$ | $R_2$ | $R_1$ | $R_2$ | $R_1$ | $R_2$ |
|---|---|---|---|---|---|
| $CH_3O$ | $CH_3$ | $C_2H_5O$ | $CH_3$ | $n-C_3H_7O$ | $CH_3$ |
| $CH_3O$ | $C_2H_5$ | $C_2H_5O$ | $C_2H_5$ | $n-C_3H_7O$ | $C_2H_5$ |
| $CH_3O$ | $n-C_3H_7$ | $C_2H_5O$ | $n-C_3H_7$ | $n-C_3H_7O$ | $n-C_3H_7$ |
| $CH_3O$ | $n-C_4H_9$ | $C_2H_5O$ | $n-C_4H_9$ | $n-C_3H_7O$ | $n-C_4H_9$ |
| $CH_3O$ | $n-C_5H_{11}$ | $C_2H_5O$ | $n-C_5H_{11}$ | $n-C_3H_7O$ | $n-C_5H_{11}$ |
| $CH_3O$ | $n-C_6H_{13}$ | $C_2H_5O$ | $n-C_6H_{13}$ | $n-C_3H_7O$ | $n-C_6H_{13}$ |
| $CH_3O$ | $n-C_7H_{15}$ | $C_2H_5O$ | $n-C_7H_{15}$ | $n-C_3H_7O$ | $n-C_7H_{15}$ |
| $CH_3O$ | H | $C_2H_5O$ | H | $n-C_3H_7O$ | H |
| $CH_3O$ | $CH_3O$ | $C_2H_5O$ | $CH_3O$ | $n-C_3H_7O$ | $CH_3O$ |
| $CH_3O$ | $C_2H_5O$ | $C_2H_5O$ | $C_2H_5O$ | $n-C_3H_7O$ | $C_2H_5O$ |
| $CH_3O$ | $n-C_3H_7O$ | $C_2H_5O$ | $n-C_3H_7O$ | $n-C_3H_7O$ | $n-C_3H_7O$ |
| $CH_3O$ | $n-C_4H_9O$ | $C_2H_5O$ | $n-C_4H_9O$ | $n-C_3H_7O$ | $n-C_4H_9O$ |
| $CH_3O$ | $n-C_5H_{11}O$ | $C_2H_5O$ | $n-C_5H_{11}O$ | $n-C_3H_7O$ | $n-C_5H_{11}O$ |
| $CH_3O$ | $n-C_6H_{13}O$ | $C_2H_5O$ | $n-C_6H_{13}O$ | $n-C_3H_7O$ | $n-C_6H_{13}O$ |
| $CH_3O$ | $n-C_7H_{15}O$ | $C_2H_5O$ | $n-C_7H_{15}O$ | $n-C_3H_7O$ | $n-C_7H_{15}O$ |
| $CH_3O$ | $n-C_8H_{17}$ | $C_2H_5O$ | $n-C_8H_{17}$ | $n-C_3H_7O$ | $n-C_8H_{17}$ |
| $CH_3O$ | $n-C_8H_{17}O$ | $C_2H_5O$ | $n-C_8H_{17}O$ | $n-C_3H_7O$ | $n-C_8H_{17}O$ |
| $CH_3O$ | $n-C_9H_{19}$ | $C_2H_5O$ | $n-C_9H_{19}$ | $n-C_3H_7O$ | $n-C_9H_{19}$ |
| $CH_3O$ | $n-C_9H_{19}O$ | $C_2H_5O$ | $n-C_9H_{19}O$ | $n-C_3H_7O$ | $n-C_9H_{19}O$ |
| $CH_3O$ | $n-C_{10}H_{21}$ | $C_2H_5O$ | $n-C_{10}H_{21}$ | $n-C_3H_7O$ | $n-C_{10}H_{21}$ |
| $CH_3O$ | $n-C_{10}H_{21}O$ | $C_2H_5O$ | $n-C_{10}H_{12}O$ | $n-C_3H_7O$ | $n-C_{10}H_{21}O$ |
| $CH_3O$ | $n-C_{11}H_{23}$ | $C_2H_5O$ | $n-C_{11}H_{23}$ | $n-C_3H_7O$ | $n-C_{11}H_{23}$ |
| $CH_3O$ | $n-C_{12}H_{25}$ | $C_2H_5O$ | $n-C_{12}H_{25}$ | $n-C_3H_7O$ | $n-C_{12}H_{25}$ |
| $R_1$ | $R_2$ | $R_4$ | $R_2$ | $R_1$ | $R_2$ |
| $n-C_4H_9O$ | $CH_3$ | $n-C_5H_{11}O$ | $CH_3$ | $n-C_6H_{13}O$ | $CH_3$ |

TABLE 3-continued

Compounds of formula

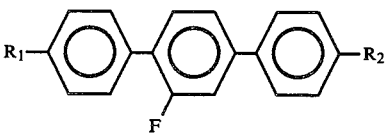

| R₁ | R₂ | R₁ | R₂ | R₁ | R₂ |
|---|---|---|---|---|---|
| n-C$_4$H$_9$O | C$_2$H$_5$ | n-C$_5$H$_{11}$O | C$_2$H$_5$ | n-C$_6$H$_{13}$O | C$_2$H$_5$ |
| n-C$_4$H$_9$O | n-C$_3$H$_7$ | n-C$_5$H$_{11}$O | n-C$_3$H$_7$ | n-C$_6$H$_{13}$O | n-C$_3$H$_7$ |
| n-C$_4$H$_9$O | n-C$_4$H$_9$ | n-C$_5$H$_{11}$O | n-C$_4$H$_9$ | n-C$_6$H$_{13}$O | n-C$_4$H$_9$ |
| n-C$_4$H$_9$O | n-C$_5$H$_{11}$ | n-C$_5$H$_{11}$O | n-C$_5$H$_{11}$ | n-C$_6$H$_{13}$O | n-C$_5$H$_{11}$ |
| n-C$_4$H$_9$O | n-C$_6$H$_{13}$ | n-C$_5$H$_{11}$O | n-C$_6$H$_{13}$ | n-C$_6$H$_{13}$O | n-C$_6$H$_{13}$ |
| n-C$_4$H$_9$O | n-C$_7$H$_{15}$ | n-C$_5$H$_{11}$O | n-C$_7$H$_{15}$ | n-C$_6$H$_{13}$O | n-C$_7$H$_{15}$ |
| n-C$_4$H$_9$O | H | n-C$_5$H$_{11}$O | H | n-C$_6$H$_{13}$O | H |
| n-C$_4$H$_9$O | CH$_3$O | n-C$_5$H$_{11}$O | CH$_3$O | n-C$_6$H$_{13}$O | CH$_3$O |
| n-C$_4$H$_9$O | C$_2$H$_5$O | n-C$_5$H$_{11}$O | C$_2$H$_5$O | n-C$_6$H$_{13}$O | C$_2$H$_5$O |
| n-C$_4$H$_9$O | n-C$_3$H$_7$O | n-C$_5$H$_{11}$O | n-C$_3$H$_7$O | n-C$_6$H$_{13}$O | n-C$_3$H$_7$O |
| n-C$_4$H$_9$O | n-C$_4$H$_9$O | n-C$_5$H$_{11}$O | n-C$_4$H$_9$O | n-C$_6$H$_{13}$O | n-C$_4$H$_9$O |
| n-C$_4$H$_9$O | n-C$_5$H$_{11}$O | n-C$_5$H$_{11}$O | n-C$_5$H$_{11}$O | n-C$_6$H$_{13}$O | n-C$_5$H$_{11}$O |
| n-C$_4$H$_9$O | n-C$_6$H$_{13}$O | n-C$_5$H$_{11}$O | n-C$_6$H$_{13}$O | n-C$_6$H$_{13}$O | n-C$_6$H$_{13}$O |
| n-C$_4$H$_9$O | n-C$_7$H$_{15}$O | n-C$_5$H$_{11}$O | n-C$_7$H$_{15}$O | n-C$_6$H$_{13}$O | n-C$_7$H$_{15}$O |
| n-C$_4$H$_9$O | n-C$_8$H$_{17}$ | n-C$_5$H$_{11}$O | n-C$_8$H$_{17}$ | n-C$_6$H$_{13}$O | n-C$_8$H$_{17}$ |
| n-C$_4$H$_9$O | n-C$_8$H$_{17}$O | n-C$_5$H$_{11}$O | n-C$_8$H$_{17}$O | n-C$_6$H$_{13}$O | n-C$_8$H$_{17}$O |
| n-C$_4$H$_9$O | n-C$_9$H$_{19}$ | n-C$_5$H$_{11}$O | n-C$_9$H$_{19}$ | n-C$_6$H$_{13}$O | n-C$_9$H$_{19}$ |
| n-C$_4$H$_9$O | n-C$_9$H$_{19}$O | n-C$_5$H$_{11}$O | n-C$_9$H$_{19}$O | n-C$_6$H$_{13}$O | n-C$_9$H$_{19}$ |
| n-C$_4$H$_9$O | n-C$_{10}$H$_{21}$ | n-C$_5$H$_{11}$O | n-C$_{10}$H$_{21}$ | n-C$_6$H$_{13}$O | n-C$_{10}$H$_{21}$ |
| n-C$_4$H$_9$O | n-C$_{10}$H$_{21}$O | n-C$_5$H$_{11}$O | n-C$_{10}$H$_{21}$O | n-C$_6$H$_{13}$O | n-C$_{10}$H$_{21}$C |
| n-C$_4$H$_9$O | n-C$_{11}$H$_{23}$ | n-C$_5$H$_{11}$O | n-C$_{11}$H$_{23}$ | n-C$_6$H$_{13}$O | n-C$_{11}$H$_{23}$ |
| n-C$_4$H$_9$O | n-C$_{12}$H$_{25}$ | n-C$_5$H$_{11}$O | n-C$_{12}$H$_{25}$ | n-C$_6$H$_{13}$O | n-C$_{12}$H$_{25}$ |
| n-C$_4$H$_9$O | n-C$_{12}$H$_{25}$O | n-C$_5$H$_{11}$O | n-C$_{12}$H$_{25}$O | n-C$_6$H$_{13}$O | n-C$_{12}$H$_{25}$O |
| R$_1$ | R$_2$ | R$_1$ | R$_2$ | R$_1$ | R$_2$ |
| n-C$_7$H$_{15}$O | CH$_3$ | n-C$_8$H$_{17}$O | CH$_3$ | n-C$_9$H$_{19}$O | CH$_3$ |
| n-C$_7$H$_{15}$O | C$_2$H$_5$ | n-C$_8$H$_{17}$O | C$_2$H$_5$ | n-C$_9$H$_{19}$O | C$_2$H$_5$ |
| n-C$_7$H$_{15}$O | n-C$_3$H$_7$ | n-C$_8$H$_{17}$O | n-C$_3$H$_7$ | n-C$_9$H$_{19}$O | n-C$_3$H$_7$ |
| n-C$_7$H$_{15}$O | n-C$_4$H$_9$ | n-C$_8$H$_{17}$O | n-C$_4$H$_9$ | n-C$_9$H$_{19}$O | n-C$_4$H$_9$ |
| n-C$_7$H$_{15}$O | n-C$_5$H$_{11}$ | n-C$_8$H$_{17}$O | n-C$_5$H$_{11}$ | n-C$_9$H$_{19}$O | n-C$_5$H$_{11}$ |
| n-C$_7$H$_{15}$O | n-C$_6$H$_{13}$ | n-C$_8$H$_{17}$O | n-C$_6$H$_{13}$ | n-C$_9$H$_{19}$O | n-C$_6$H$_{13}$ |
| n-C$_7$H$_{15}$O | n-C$_7$H$_{15}$ | n-C$_8$H$_{17}$O | n-C$_7$H$_{15}$ | n-C$_9$H$_{19}$O | n-C$_7$H$_{15}$ |
| n-C$_7$H$_{15}$O | H | n-C$_8$H$_{17}$O | n-C$_8$H$_{17}$ | n-C$_9$H$_{19}$O | n-C$_8$H$_{17}$ |
| n-C$_7$H$_{15}$O | CH$_3$O | n-C$_8$H$_{17}$O | CH$_3$O | n-C$_9$H$_{19}$O | H |
| n-C$_7$H$_{15}$O | C$_2$H$_5$O | n-C$_8$H$_{17}$O | C$_2$H$_5$O | n-C$_9$H$_{19}$O | CH$_3$O |
| n-C$_7$H$_{15}$O | n-C$_3$H$_7$O | n-C$_8$H$_{17}$O | n-C$_3$H$_7$O | n-C$_9$H$_{19}$O | C$_2$H$_5$O |
| n-C$_7$H$_{15}$O | n-C$_4$H$_9$O | n-C$_8$H$_{17}$O | n-C$_4$H$_9$O | n-C$_9$H$_{19}$O | n-C$_3$H$_7$O |
| n-C$_7$H$_{15}$O | n-C$_5$H$_{11}$O | n-C$_8$H$_{17}$O | n-C$_5$H$_{11}$O | n-C$_9$H$_{19}$O | n-C$_4$H$_9$O |
| n-C$_7$H$_{15}$O | n-C$_6$H$_{13}$O | n-C$_8$H$_{17}$O | n-C$_6$H$_{13}$O | n-C$_9$H$_{19}$O | n-C$_5$H$_{11}$O |
| n-C$_7$H$_{15}$O | n-C$_7$H$_{15}$O | n-C$_8$H$_{17}$O | n-C$_7$H$_{15}$O | n-C$_9$H$_{19}$O | n-C$_6$H$_{13}$O |
| n-C$_7$H$_{15}$O | n-C$_8$H$_{17}$ | n-C$_8$H$_{17}$O | n-C$_8$H$_{17}$O | n-C$_9$H$_{19}$O | n-C$_7$H$_{15}$O |
| n-C$_7$H$_{15}$O | n-C$_8$H$_{17}$O | n-C$_8$H$_{17}$O | n-C$_9$H$_{19}$ | n-C$_9$H$_{19}$O | n-C$_8$H$_{17}$O |
| n-C$_7$H$_{15}$O | n-C$_9$H$_{19}$ | n-C$_8$H$_{17}$O | n-C$_9$H$_{19}$O | n-C$_9$H$_{19}$O | n-C$_9$H$_{19}$ |
| n-C$_7$H$_{15}$O | n-C$_9$H$_{19}$O | n-C$_8$H$_{17}$O | n-C$_{10}$H$_{21}$ | n-C$_9$H$_{19}$O | n-C$_9$H$_{19}$O |
| n-C$_7$H$_{15}$O | n-C$_{10}$H$_{21}$ | n-C$_8$H$_{17}$O | n-C$_{10}$H$_{21}$O | n-C$_9$H$_{19}$O | n-C$_{10}$H$_{21}$ |
| n-C$_7$H$_{15}$O | n-C$_{10}$H$_{21}$O | n-C$_8$H$_{17}$O | n-C$_{11}$H$_{23}$ | n-C$_9$H$_{19}$O | n-C$_{10}$H$_{21}$O |
| n-C$_7$H$_{15}$O | n-C$_{11}$H$_{23}$ | n-C$_8$H$_{17}$O | n-C$_{12}$H$_{25}$ | n-C$_9$H$_{19}$O | n-C$_{11}$H$_{23}$ |
| n-C$_7$H$_{15}$O | n-C$_{12}$H$_{25}$ | n-C$_8$H$_{17}$O | n-C$_{12}$H$_{25}$O | n-C$_9$H$_{19}$O | n-C$_{12}$H$_{25}$O |
| n-C$_7$H$_{15}$O | n-C$_{12}$H$_{25}$O | | | | |
| n-C$_{10}$H$_{21}$O | CH$_3$ | n-C$_{11}$H$_{23}$O | CH$_3$ | n-C$_{12}$H$_{25}$O | CH$_3$ |
| n-C$_{10}$H$_{21}$O | C$_2$H$_5$ | n-C$_{11}$H$_{23}$O | C$_2$H$_5$ | n-C$_{12}$H$_{25}$O | C$_2$H$_5$ |
| n-C$_{10}$H$_{21}$O | n-C$_3$H$_7$ | n-C$_{11}$H$_{23}$O | n-C$_3$H$_7$ | n-C$_{12}$H$_{25}$O | n-C$_3$H$_7$ |
| n-C$_{10}$H$_{21}$O | n-C$_4$H$_9$ | n-C$_{11}$H$_{23}$O | n-C$_4$H$_9$ | n-C$_{12}$H$_{25}$O | n-C$_4$H$_9$ |
| n-C$_{10}$H$_{21}$O | n-C$_5$H$_{11}$ | n-C$_{11}$H$_{23}$O | n-C$_5$H$_{11}$ | n-C$_{12}$H$_{25}$O | n-C$_5$H$_{11}$ |
| n-C$_{10}$H$_{21}$O | n-C$_6$H$_{13}$ | n-C$_{11}$H$_{23}$O | n-C$_6$H$_{13}$ | n-C$_{12}$H$_{25}$O | n-C$_6$H$_{13}$ |
| n-C$_{10}$H$_{21}$O | n-C$_7$H$_{15}$ | n-C$_{11}$H$_{23}$O | n-C$_7$H$_{15}$ | n-C$_{12}$H$_{25}$O | n-C$_7$H$_{15}$ |
| n-C$_{10}$H$_{21}$O | n-C$_8$H$_{17}$ | n-C$_{11}$H$_{23}$O | n-C$_8$H$_{17}$ | n-C$_{12}$H$_{25}$O | n-C$_8$H$_{17}$ |
| n-C$_{10}$H$_{21}$O | n-C$_9$H$_{19}$ | n-C$_{11}$H$_{23}$O | n-C$_9$H$_{19}$ | n-C$_{12}$H$_{25}$O | n-C$_9$H$_{19}$ |
| n-C$_{10}$H$_{21}$O | n-C$_{10}$H$_{21}$ | n-C$_{11}$H$_{23}$O | n-C$_{10}$H$_{21}$ | n-C$_{12}$H$_{25}$O | n-C$_{10}$H$_{21}$ |
| n-C$_{10}$H$_{21}$O | n-C$_{11}$H$_{23}$ | n-C$_{11}$H$_{23}$O | n-C$_{11}$H$_{23}$ | n-C$_{12}$H$_{25}$O | n-C$_{11}$H$_{23}$ |
| n-C$_{10}$H$_{21}$O | n-C$_{12}$H$_{25}$ | n-C$_{11}$H$_{23}$O | n-C$_{12}$H$_{25}$ | n-C$_{12}$H$_{25}$O | n-C$_{12}$H$_{25}$ |
| n-C$_{10}$H$_{21}$O | H | n-C$_{11}$H$_{23}$O | H | n-C$_{12}$H$_{25}$O | H |
| n-C$_{10}$H$_{21}$O | CH$_3$O | n-C$_{11}$H$_{23}$O | CH$_3$O | n-C$_{12}$H$_{25}$O | CH$_3$O |
| n-C$_{10}$H$_{21}$O | C$_2$H$_5$O | n-C$_{11}$H$_{23}$O | C$_2$H$_5$O | n-C$_{12}$H$_{25}$O | C$_2$H$_5$O |
| n-C$_{10}$H$_{21}$O | n-C$_3$H$_7$O | n-C$_{11}$H$_{23}$O | n-C$_3$H$_7$O | n-C$_{12}$H$_{25}$O | n-C$_3$H$_7$O |
| n-C$_{10}$H$_{21}$O | n-C$_4$H$_9$O | n-C$_{11}$H$_{23}$O | n-C$_4$H$_9$0 | n-C$_{12}$H$_{25}$O | n-C$_4$H$_9$O |
| n-C$_{10}$H$_{21}$O | n-C$_5$H$_{11}$O | n-C$_{11}$H$_{23}$O | n-C$_5$H$_{11}$O | n-C$_{12}$H$_{25}$O | n-C$_5$H$_{11}$O |
| n-C$_{10}$H$_{21}$O | n-C$_6$H$_{13}$O | n-C$_{11}$H$_{23}$O | n-C$_6$H$_{13}$O | n-C$_{12}$H$_{25}$O | n-C$_6$H$_{13}$O |
| n-C$_{10}$H$_{21}$O | n-C$_7$H$_{15}$O | n-C$_{11}$H$_{23}$O | n-C$_7$H$_{15}$O | n-C$_{12}$H$_{25}$O | n-C$_7$H$_{15}$O |
| n-C$_{10}$H$_{21}$O | n-C$_8$H$_{17}$O | n-C$_{11}$H$_{23}$O | n-C$_8$H$_{17}$O | n-C$_{12}$H$_{25}$O | n-C$_8$H$_{17}$O |
| n-C$_{10}$H$_{21}$O | n-C$_9$H$_{19}$O | n-C$_{11}$H$_{23}$O | n-C$_{19}$H$_{19}$O | n-C$_{12}$H$_{25}$O | n-C$_9$H$_{19}$O |
| n-C$_{10}$H$_{21}$O | n-C$_{10}$H$_{21}$O | n-C$_{11}$H$_{23}$O | n-C$_{10}$H$_{21}$O | n-C$_{12}$H$_{25}$O | n-C$_{10}$H$_{21}$O |

TABLE 3-continued

Compounds of formula

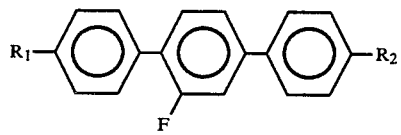

| n-C$_{10}$H$_{21}$O | n-C$_{12}$H$_{25}$O | n-C$_{11}$H$_{23}$O | n-C$_{12}$H$_{25}$O | n-C$_{12}$H$_{25}$O | n-C$_{12}$H$_{25}$O |
|---|---|---|---|---|---|

EXAMPLE 3

An example of Route C specified above wherein R$_1$=n-C$_5$H$_{11}$ and R$_2$=n-C$_3$H$_7$.

Step C1

The preparation of 4'-n-pentanoyl-4-brono-2-fluorobiphenyl.

The procedure carried out in Step C1 was similar to that described in Step A4 above.

Step C2

The preparation of 4'-n-pentyl-4-bromo-2-fluorobiphenyl.

The ketone produced by Step C1 was reduced using the standard LiAlH$_4$-AlCl$_3$/(C$_2$H$_5$)$_2$O/CHCl$_3$ method from the literature described in J. Org. Chem. 37, 3355 (1972) by W. L. Albrecht, D. H. Gustafson and S. W. Horgan. Any resulting alkene was hydrogenated using 10% Pt-C/hydrogen (H$_2$) in ethyl acetate:

4'-n-pentyl-4-bromo-2-fluorobiphenyl, bp=110° C./0.01 mmHg, was the product obtained by this procedure.

Step C3

The method of preparing cis/trans-4-n-Pentyl-1-(4"-n-propyl-2'-fluorobiphenyl-4'-yl)cyclohexanol was similar to that described in Step A1 above.

The isomeric compounds prepared by Step C3 are given in Table 4 below:

TABLE 4

Compounds of formula

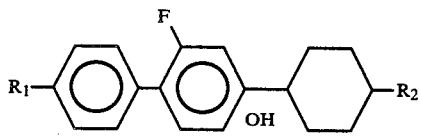

Transition Temperatures (°C.)

| R$_1$ | R$_2$ | | C—S | S—N | N—I |
|---|---|---|---|---|---|
| n-C$_5$H$_{11}$ | n-C$_3$H$_7$ | cis isomer | 79.5 | | |
| n-C$_5$H$_{11}$ | n-C$_3$H$_7$ | trans isomer | 58.0 | 86.0 | 113.2 |

The mp's and transition temperatures were confirmed by DSC.

Step C4

The method of preparation of 4-n-pentyl-1-1-4"-n-propyl-1-2'-fluorobiphenyl-4'-yl)cyclohexenes was similar to that described in Step A2 above.

Step C5

The product of Step C4 was converted into the corresponding 2'-fluoro-4-n-pentyl-4"-n-propyl-p-terphenyl by a procedure similar to Step A3 above.

Compounds which may be prepared by an analogous procedure are as listed in Table 2 above.

Further examples of the products of Steps C1 to C5 are as listed in Table 5 as follows:

TABLE 5

Compounds wherein R$_1$ = n-C$_3$H$_7$, R$_2$ = n-C$_5$H$_{11}$

| Product of Step C1 | | |
|---|---|---|
| R$_1$ | R$_2$ | mp (°C.) |
| C$_2$H$_5$ | — | 94 |

| Product of Step C2 | | |
|---|---|---|
| R$_1$ | R$_2$ | bp (°C./0.01 mmHg) |
| n-C$_3$H$_7$ | — | 130 |

| Product of Step C3 | | | | |
|---|---|---|---|---|
| R$_1$ | R$_2$ | | mp (°C.) | S-N (°C.) | N-I (°C.) |
| n-C$_3$H$_7$ | n-C$_5$H$_{11}$ | cis isomer | 88.0 | | |
| n-C$_3$H$_7$ | | trans isomer | 58.0 | 116.5 | 123.0 |

*assignment based on the liquid crystal behaviour of this compound.

EXAMPLE 4

An example of Route D specified above wherein R$_1$=n-C$_4$H$_9$ and R$_2$=n-C$_3$H$_7$.

Step D1

The method of preparation of 4-bromo-2-fluoro-4'-hydroxybiphenyl was similar to that described in Step B1 above.

Step D2

The method of preparation of 4-bromo-4'-butoxy-2-fluorobiphenyl was similar to that described in Step B2 above.

Step D3

The method of preparation of cis/trans-4-n-butoxy-1-(4"-n-propyl-2'-fluorobiphenyl-4'-yl)cyclohexanol was similar to that described in Step A1 above.

Step D4

The method of preparation of 4-n-butoxy-1-14"-n-propyl-2'-fluorobiphenyl-4'-yl)cyclohexene was similar to that described in Step A2 above.

Step D5

The method of preparation of 2'-fluoro-4-n-butoxy-4"-n-propyl-p-terphenyl was similar to that described in Step A3 above.

The fluoro-p-terphenyl compounds which may be prepared analogously to Steps D1–D5 are as listed in Table 3 above.

As mentioned above, compounds of Formula I which are 2-fluoro compounds may be prepared by methods analogous to Examples 1, 2, 3 or 4 using the appropriate 2-fluoro starting material. Examples of 2-fluoro compounds which may be made in this way are listed in Table 6 as follows.

TABLE 6

Compounds of formula:

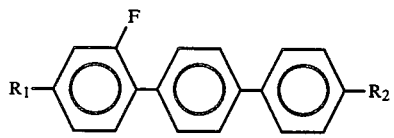

| R₁ | R₂ | R₁ | R₂ | R₁ | R₂ |
|---|---|---|---|---|---|
| CH₃ | CH₃ | C₂H₅ | CH₃ | n-C₃H₇ | CH₃ |
| CH₃ | C₂H₅ | C₂H₅ | C₂H₅ | n-C₃H₇ | C₂H₅ |
| CH₃ | n-C₃H₇ | C₂H₅ | n-C₃H₇ | n-C₃H₇ | n-C₃H₇ |
| CH₃ | n-C₄H₉ | C₂H₅ | n-C₄H₉ | n-C₃H₇ | n-C₄H₉ |
| CH₃ | n-C₅H₁₁ | C₂H₅ | n-C₅H₁₁ | n-C₃H₇ | n-C₅H₁₁ |
| CH₃ | n-C₆H₁₃ | C₂H₅ | n-C₆H₁₃ | n-C₃H₇ | n-C₆H₁₃ |
| CH₃ | n-C₇H₁₅ | C₂H₅ | n-C₇H₁₅ | n-C₃H₇ | n-C₇H₁₅ |
| CH₃ | H | C₂H₅ | H | n-C₃H₇ | H |
| CH₃ | CH₃O | C₂H₅ | CH₃O | n-C₃H₇ | CH₃O |
| CH₃ | C₂H₅O | C₂H₅ | C₂H₅O | n-C₃H₇ | C₂H₅O |
| CH₃ | n-C₃H₇O | C₂H₅ | n-C₃H₇O | n-C₃H₇ | n-C₃H₇O |
| CH₃ | n-C₄H₉O | C₂H₅ | n-C₄H₉O | n-C₃H₇ | n-C₄H₉O |
| CH₃ | n-C₅H₁₁O | C₂H₅ | n-C₅H₁₁O | n-C₃H₇ | n-C₅H₁₁O |
| CH₃ | n-C₆H₁₃O | C₂H₅ | n-C₆H₁₃O | n-C₃H₇ | n-C₆H₁₃O |
| CH₃ | n-C₇H₁₅O | C₂H₅ | n-C₇H₁₅O | n-C₃H₇ | n-C₇H₁₅O |
| CH₃ | n-C₈H₁₇ | C₂H₅ | n-C₈H₁₇ | n-C₃H₇ | n-C₈H₁₇ |
| CH₃ | n-C₈H₁₇O | C₂H₅ | n-C₈H₁₇O | n-C₃H₇ | n-C₈H₁₇O |
| CH₃ | n-C₉H₁₉ | C₂H₅ | n-C₉H₁₉ | n-C₃H₇ | n-C₉H₁₉ |
| CH₃ | n-C₉H₁₉O | C₂H₅ | n-C₉H₁₉O | n-C₃H₇ | n-C₉H₁₉O |
| CH₃ | n-C₁₀H₂₁ | C₂H₅ | n-C₁₀H₂₁ | n-C₃H₇ | n-C₁₀H₂₁ |
| CH₃ | n-C₁₀H₂₁O | C₂H₅ | n-C₁₀H₁₂O | n-C₃H₇ | n-C₁₀H₂₁O |
| CH₃ | n-C₁₁H₂₃ | C₂H₅ | n-C₁₁H₂₃ | n-C₃H₇ | n-C₁₁H₂₃ |
| CH₃ | n-C₁₂H₂₅ | C₂H₅ | n-C₁₂H₂₅ | n-C₃H₇ | n-C₁₂H₂₅ |

| R₁ | R₂ | R₄ | R₂ | R₁ | R₂ |
|---|---|---|---|---|---|
| n-C₄H₉ | CH₃ | n-C₅H₁₁ | CH₃ | n-C₆H₁₃ | CH₃ |
| n-C₄H₉ | C₂H₅ | n-C₅H₁₁ | C₂H₅ | n-C₆H₁₃ | C₂H₅ |
| n-C₄H₉ | n-C₃H₇ | n-C₅H₁₁ | n-C₃H₇ | n-C₆H₁₃ | n-C₃H₇ |
| n-C₄H₉ | n-C₄H₉ | n-C₅H₁₁ | n-C₄H₉ | n-C₆H₁₃ | n-C₄H₉ |
| n-C₄H₉ | n-C₅H₁₁ | n-C₅H₁₁ | n-C₅H₁₁ | n-C₆H₁₃ | n-C₅H₁₁ |
| n-C₄H₉ | n-C₆H₁₃ | n-C₅H₁₁ | n-C₆H₁₃ | n-C₆H₁₃ | n-C₆H₁₃ |
| n-C₄H₉ | n-C₇H₁₅ | n-C₅H₁₁ | n-C₇H₁₅ | n-C₆H₁₃ | n-C₇H₁₅ |
| n-C₄H₉ | H | n-C₅H₁₁ | H | n-C₆H₁₃ | H |
| n-C₄H₉ | CH₃O | n-C₅H₁₁ | CH₃O | n-C₆H₁₃ | CH₃O |
| n-C₄H₉ | C₂H₅O | n-C₅H₁₁ | C₂H₅O | n-C₆H₁₃ | C₂H₅O |
| n-C₄H₉ | n-C₃H₇O | n-C₅H₁₁ | n-C₃H₇O | n-C₆H₁₃ | n-C₃H₇O |
| n-C₄H₉ | n-C₄H₉O | n-C₅H₁₁ | n-C₄H₉O | n-C₆H₁₃ | n-C₄H₉O |
| n-C₄H₉ | n-C₅H₁₁O | n-C₅H₁₁ | n-C₅H₁₁O | n-C₆H₁₃ | n-C₅H₁₁O |
| n-C₄H₉ | n-C₆H₁₃O | n-C₅H₁₁ | n-C₆H₁₃O | n-C₆H₁₃ | n-C₆H₁₃O |
| n-C₄H₉ | n-C₇H₁₅O | n-C₅H₁₁ | n-C₇H₁₅O | n-C₆H₁₃ | n-C₇H₁₅O |
| n-C₄H₉ | n-C₈H₁₇ | n-C₅H₁₁ | n-C₈H₁₇ | n-C₆H₁₃ | n-C₈H₁₇ |
| n-C₄H₉ | n-C₈H₁₇O | n-C₅H₁₁ | n-C₈H₁₇O | n-C₆H₁₃ | n-C₈H₁₇O |
| n-C₄H₉ | n-C₉H₁₉ | n-C₅H₁₁ | n-C₉H₁₉ | n-C₆H₁₃ | n-C₉H₁₉ |
| n-C₄H₉ | n-C₉H₁₉O | n-C₅H₁₁ | n-C₉H₁₉O | n-C₆H₁₃ | n-C₉H₁₉ |
| n-C₄H₉ | n-C₁₀H₂₁ | n-C₅H₁₁ | n-C₁₀H₂₁ | n-C₆H₁₃ | n-C₁₀H₂₁ |
| n-C₄H₉ | n-C₁₀H₂₁O | n-C₅H₁₁ | n-C₁₀H₂₁O | n-C₆H₁₃ | n-C₁₀H₂₁O |
| n-C₄H₉ | n-C₁₁H₂₃ | n-C₅H₁₁ | n-C₁₁H₂₃ | n-C₆H₁₃ | n-C₁₁H₂₃ |
| n-C₄H₉ | n-C₁₂H₂₅ | n-C₅H₁₁ | n-C₁₂H₂₅ | n-C₆H₁₃ | n-C₁₂H₂₅ |
| n-C₄H₉ | n-C₁₂H₂₅O | n-C₅H₁₁ | n-C₁₂H₂₅O | n-C₆H₁₃ | n-C₁₂H₂₅O |

| R₁ | R₂ | R₁ | R₂ | R₁ | R₂ |
|---|---|---|---|---|---|
| n-C₇H₁₅ | CH₃ | n-C₈H₁₇ | CH₃ | n-C₉H₁₉ | CH₃ |
| n-C₇H₁₅ | C₂H₅ | n-C₈H₁₇ | C₂H₅ | n-C₉H₁₉ | C₂H₅ |
| n-C₇H₁₅ | n-C₃H₇ | n-C₈H₁₇ | n-C₃H₇ | n-C₉H₁₉ | n-C₃H₇ |
| n-C₇H₁₅ | n-C₄H₉ | n-C₈H₁₇ | n-C₄H₉ | n-C₉H₁₉ | n-C₄H₉ |
| n-C₇H₁₅ | n-C₅H₁₁ | n-C₈H₁₇ | n-C₅H₁₁ | n-C₉H₁₉ | n-C₅H₁₁ |
| n-C₇H₁₅ | n-C₆H₁₃ | n-C₈H₁₇ | n-C₆H₁₃ | n-C₉H₁₉ | n-C₆H₁₃ |
| n-C₇H₁₅ | n-C₇H₁₅ | n-C₈H₁₇ | n-C₇H₁₅ | n-C₉H₁₉ | n-C₇H₁₅ |
| n-C₇H₁₅ | H | n-C₈H₁₇ | n-C₈H₁₇ | n-C₉H₁₉ | n-C₈H₁₇ |
| n-C₇H₁₅ | CH₃O | n-C₈H₁₇ | CH₃O | n-C₉H₁₉ | H |
| n-C₇H₁₅ | C₂H₅O | n-C₈H₁₇ | C₂H₅O | n-C₉H₁₉ | CH₃O |
| n-C₇H₁₅ | n-C₃H₇O | n-C₈H₁₇ | n-C₃H₇O | n-C₉H₁₉ | C₂H₅O |
| n-C₇H₁₅ | n-C₄H₉O | n-C₈H₁₇ | n-C₄H₉O | n-C₉H₁₉ | n-C₃H₇O |
| n-C₇H₁₅ | n-C₅H₁₁O | n-C₈H₁₇ | n-C₅H₁₁O | n-C₉H₁₉ | n-C₄H₉O |
| n-C₇H₁₅ | n-C₆H₁₃O | n-C₈H₁₇ | n-C₆H₁₃O | n-C₉H₁₉ | n-C₅H₁₁O |
| n-C₇H₁₅ | n-C₇H₁₅O | n-C₈H₁₇ | n-C₇H₁₅O | n-C₉H₁₉ | n-C₆H₁₃O |
| n-C₇H₁₅ | n-C₈H₁₇ | n-C₈H₁₇ | n-C₈H₁₇O | n-C₉H₁₉ | n-C₇H₁₅O |
| n-C₇H₁₅ | n-C₈H₁₇O | n-C₈H₁₇ | n-C₉H₁₉ | n-C₉H₁₉ | n-C₈H₁₇O |
| n-C₇H₁₅ | n-C₉H₁₉ | n-C₈H₁₇ | n-C₉H₁₉O | n-C₉H₁₉ | n-C₉H₁₉ |

TABLE 6-continued

Compounds of formula:

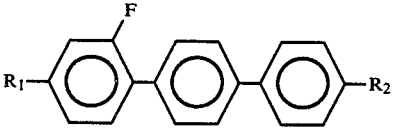

| | | | | | |
|---|---|---|---|---|---|
| n-C$_7$H$_{15}$ | n-C$_9$H$_{19}$O | n-C$_8$H$_{17}$ | n-C$_{10}$H$_{21}$ | n-C$_9$H$_{19}$ | n-C$_9$H$_{19}$O |
| n-C$_7$H$_{15}$ | n-C$_{10}$H$_{21}$ | n-C$_8$H$_{17}$ | n-C$_{10}$H$_{21}$O | n-C$_9$H$_{19}$ | n-C$_{10}$H$_{21}$ |
| n-C$_7$H$_{15}$ | n-C$_{10}$H$_{21}$O | n-C$_8$H$_{17}$ | n-C$_{11}$H$_{23}$ | n-C$_9$H$_{19}$ | n-C$_{10}$H$_{21}$O |
| n-C$_7$H$_{15}$ | n-C$_{11}$H$_{23}$ | n-C$_8$H$_{17}$ | n-C$_{12}$H$_{25}$ | n-C$_9$H$_{19}$ | n-C$_{11}$H$_{23}$ |
| n-C$_7$H$_{15}$ | n-C$_{12}$H$_{25}$ | n-C$_8$H$_{17}$ | n-C$_{12}$H$_{25}$O | n-C$_9$H$_{19}$ | n-C$_{12}$H$_{25}$ |
| n-C$_7$H$_{15}$ | n-C$_{12}$H$_{25}$O | | | | |
| n-C$_{10}$H$_{21}$ | CH$_3$ | n-C$_{11}$H$_{23}$ | CH$_3$ | n-C$_{12}$H$_{25}$ | CH$_3$ |
| n-C$_{10}$H$_{21}$ | C$_2$H$_5$ | n-C$_{11}$H$_{23}$ | C$_2$H$_5$ | n-C$_{12}$H$_{25}$ | C$_2$H$_5$ |
| n-C$_{10}$H$_{21}$ | n-C$_3$H$_7$ | n-C$_{11}$H$_{23}$ | n-C$_3$H$_7$ | n-C$_{12}$H$_{25}$ | n-C$_3$H$_7$ |
| n-C$_{10}$H$_{21}$ | n-C$_4$H$_9$ | n-C$_{11}$H$_{23}$ | n-G$_4$H$_9$ | n-C$_{12}$H$_{25}$ | n-C$_4$H$_9$ |
| n-C$_{10}$H$_{21}$ | n-C$_5$H$_{11}$ | n-C$_{11}$H$_{23}$ | n-C$_5$H$_{11}$ | n-C$_{12}$H$_{25}$ | n-C$_5$H$_{11}$ |
| n-C$_{10}$H$_{21}$ | n-C$_6$H$_{13}$ | n-C$_{11}$H$_{23}$ | n-C$_6$H$_{13}$ | n-C$_{12}$H$_{25}$ | n-C$_6$H$_{13}$ |
| n-C$_{10}$H$_{21}$ | n-C$_7$H$_{15}$ | n-C$_{11}$H$_{23}$ | n-C$_7$H$_{15}$ | n-C$_{12}$H$_{25}$ | n-C$_7$H$_{15}$ |
| n-C$_{10}$H$_{21}$ | n-C$_8$H$_{17}$ | n-C$_{11}$H$_{23}$ | n-C$_8$H$_{17}$ | n-C$_{12}$H$_{25}$ | n-C$_8$H$_{17}$ |
| n-C$_{10}$H$_{21}$ | n-C$_9$H$_{19}$ | n-C$_{11}$H$_{23}$ | n-C$_9$H$_{19}$ | n-C$_{12}$H$_{25}$ | n-C$_9$H$_{19}$ |
| n-C$_{10}$H$_{21}$ | n-C$_{10}$H$_{21}$ | n-C$_{11}$H$_{23}$ | n-C$_{10}$H$_{21}$ | n-C$_{12}$H$_{25}$ | n-C$_{10}$H$_{21}$ |
| n-C$_{10}$H$_{21}$ | n-C$_{11}$H$_{23}$ | n-C$_{11}$H$_{23}$ | n-C$_{11}$H$_{23}$ | n-C$_{12}$H$_{25}$ | n-C$_{11}$H$_{23}$ |
| n-C$_{10}$H$_{21}$ | n-C$_{12}$H$_{25}$ | n-C$_{11}$H$_{23}$ | n-C$_{12}$H$_{25}$ | n-C$_{12}$H$_{25}$ | n-C$_{12}$H$_{25}$ |
| n-C$_{10}$H$_{21}$ | H | n-C$_{11}$H$_{23}$ | H | n-C$_{12}$H$_{25}$ | H |
| n-C$_{10}$H$_{21}$ | CH$_3$O | n-C$_{11}$H$_{23}$ | CH$_3$O | n-C$_{12}$H$_{25}$ | CH$_3$O |
| n-C$_{10}$H$_{21}$ | C$_2$H$_5$O | n-C$_{11}$H$_{23}$ | C$_2$H$_5$O | n-C$_{12}$H$_{25}$ | C$_2$H$_5$O |
| n-C$_{10}$H$_{21}$ | n-C$_3$H$_7$O | n-C$_{11}$H$_{23}$ | n-C$_3$H$_7$O | n-C$_{12}$H$_{25}$ | n-C$_3$H$_7$O |
| n-C$_{10}$H$_{21}$ | n-C$_4$H$_9$O | n-C$_{11}$H$_{23}$ | n-C$_4$H$_9$O | n-C$_{12}$H$_{25}$ | n-C$_4$H$_9$O |
| n-C$_{10}$H$_{21}$ | n-C$_5$H$_{11}$O | n-C$_{11}$H$_{23}$ | n-C$_5$H$_{11}$O | n-C$_{12}$H$_{25}$ | n-C$_5$H$_{11}$O |
| n-C$_{10}$H$_{21}$ | n-C$_6$H$_{13}$O | n-C$_{11}$H$_{23}$ | n-C$_6$H$_{13}$O | n-C$_{12}$H$_{25}$ | n-C$_6$H$_{13}$O |
| n-C$_{10}$H$_{21}$ | n-C$_7$H$_{15}$O | n-C$_{11}$H$_{23}$ | n-C$_7$H$_{15}$O | n-C$_{12}$H$_{25}$ | n-C$_7$H$_{15}$O |
| n-C$_{10}$H$_{21}$ | n-C$_8$H$_{17}$O | n-C$_{11}$H$_{23}$ | n-C$_8$H$_{17}$O | n-C$_{12}$H$_{25}$ | n-C$_8$H$_{17}$O |
| n-C$_{10}$H$_{21}$ | n-C$_9$H$_{19}$O | n-C$_{11}$H$_{23}$ | n-C$_{19}$H$_{19}$O | n-C$_{12}$H$_{25}$ | n-C$_9$H$_{19}$O |
| n-C$_{10}$H$_{21}$ | n-C$_{10}$H$_{21}$O | n-C$_{11}$H$_{23}$ | n-C$_{10}$H$_{21}$O | n-C$_{12}$H$_{25}$ | n-C$_{10}$H$_{21}$O |
| n-C$_{10}$H$_{21}$ | n-C$_{12}$H$_{25}$O | n-C$_{12}$H$_{23}$ | n-C$_{12}$H$_{25}$O | n-C$_{12}$H$_{25}$ | n-C$_{12}$H$_{25}$O |
| CH$_3$O | CH$_3$ | C$_2$H$_5$O | CH$_3$ | n-C$_3$H$_7$O | CH$_3$ |
| CH$_3$O | C$_2$H$_5$ | C$_2$H$_5$O | C$_2$H$_5$ | n-C$_3$H$_7$O | C$_2$H$_5$ |
| CH$_3$O | n-C$_3$H$_7$ | C$_2$H$_5$O | n-C$_3$H$_7$ | n-C$_3$H$_7$O | n-C$_3$H$_7$ |
| CH$_3$O | n-C$_4$H$_9$ | C$_2$H$_5$O | n-C$_4$H$_9$ | n-C$_3$H$_7$O | n-C$_4$H$_9$ |
| CH$_3$O | n-C$_5$H$_{11}$ | C$_2$H$_5$O | n-C$_5$H$_{11}$ | n-C$_3$H$_7$O | n-C$_5$H$_{11}$ |
| CH$_3$O | n-C$_6$H$_{13}$ | C$_2$H$_5$O | n-C$_6$H$_{13}$ | n-C$_3$H$_7$O | n-C$_6$H$_{13}$ |
| CH$_3$O | n-C$_7$H$_{15}$ | C$_2$H$_5$O | n-C$_7$H$_{15}$ | n-C$_3$H$_7$O | n-C$_7$H$_{15}$ |
| CH$_3$O | H | C$_2$H$_5$O | H | n-C$_3$H$_7$O | H |
| CH$_3$O | CH$_3$O | C$_2$H$_5$O | CH$_3$O | n-C$_3$H$_7$O | CH$_3$O |
| CH$_3$O | C$_2$H$_5$O | C$_2$H$_5$O | C$_2$H$_5$O | n-C$_3$H$_7$O | C$_2$H$_5$O |
| CH$_3$O | n-C$_3$H$_7$O | C$_2$H$_5$O | n-C$_3$H$_7$O | n-C$_3$H$_7$O | n-C$_3$H$_7$O |
| CH$_3$O | n-C$_4$H$_9$O | C$_2$H$_5$O | n-C$_4$H$_9$O | n-C$_3$H$_7$O | n-C$_4$H$_9$O |
| CH$_3$O | n-C$_5$H$_{11}$O | C$_2$H$_5$O | n-C$_5$H$_{11}$O | n-C$_3$H$_7$O | n-C$_5$H$_{11}$O |
| CH$_3$O | n-C$_6$H$_{13}$O | C$_2$H$_5$O | n-C$_6$H$_{13}$O | n-C$_3$H$_7$O | n-C$_6$H$_{13}$O |
| CH$_3$O | n-C$_7$H$_{15}$O | C$_2$H$_5$O | n-C$_7$H$_{15}$O | n-C$_3$H$_7$O | n-C$_7$H$_{15}$O |
| CH$_3$O | n-C$_8$H$_{17}$ | C$_2$H$_5$O | n-C$_8$H$_{17}$ | n-C$_3$H$_7$O | n-C$_8$H$_{17}$ |
| CH$_3$O | n-C$_8$H$_{17}$O | C$_2$H$_5$O | n-C$_8$H$_{17}$O | n-C$_3$H$_7$O | n-C$_8$H$_{17}$O |
| CH$_3$O | n-C$_9$H$_{19}$ | C$_2$H$_5$O | n-C$_9$H$_{19}$ | n-C$_3$H$_7$O | n-C$_9$H$_{19}$ |
| CH$_3$O | n-C$_9$H$_{19}$O | C$_2$H$_5$O | n-C$_9$H$_{19}$O | n-C$_3$H$_7$O | n-C$_9$H$_{19}$O |
| CH$_3$O | n-C$_{10}$H$_{21}$ | C$_2$H$_5$O | n-C$_{10}$H$_{21}$ | n-C$_3$H$_7$O | n-C$_{10}$H$_{21}$ |
| CH$_3$O | n-C$_{10}$H$_{21}$O | C$_2$H$_5$O | n-C$_{10}$H$_{12}$O | n-C$_3$H$_7$O | n-C$_{10}$H$_{21}$O |
| CH$_3$O | n-C$_{11}$H$_{23}$ | C$_2$H$_5$O | n-C$_{11}$H$_{23}$ | n-C$_3$H$_7$O | n-C$_{11}$H$_{23}$ |
| CH$_3$O | n-C$_{12}$H$_{25}$ | C$_2$H$_5$O | n-C$_{12}$H$_{25}$ | n-C$_3$H$_7$O | n-C$_{12}$H$_{25}$ |

| R$_1$ | R$_2$ | R$_4$ | R$_2$ | R$_1$ | R$_2$ |
|---|---|---|---|---|---|
| n-C$_4$H$_9$O | CH$_3$ | n-C$_5$H$_{11}$O | CH$_3$ | n-C$_6$H$_{13}$O | CH$_3$ |
| n-C$_4$H$_9$O | C$_2$H$_5$ | n-C$_5$H$_{11}$O | C$_2$H$_5$ | n-C$_6$H$_{13}$O | C$_2$H$_5$ |
| n-C$_4$H$_9$O | n-C$_3$H$_7$ | n-C$_5$H$_{11}$O | n-C$_3$H$_7$ | n-C$_6$H$_{13}$O | n-C$_3$H$_7$ |
| n-C$_4$H$_9$O | n-C$_4$H$_9$ | n-C$_5$H$_{11}$O | n-C$_4$H$_9$ | n-C$_6$H$_{13}$O | n-C$_4$H$_9$ |
| n-C$_4$H$_9$O | n-C$_5$H$_{11}$ | n-C$_5$H$_{11}$O | n-C$_5$H$_{11}$ | n-C$_6$H$_{13}$O | n-C$_5$H$_{11}$ |
| n-C$_4$H$_9$O | n-C$_6$H$_{13}$ | n-C$_5$H$_{11}$O | n-C$_6$H$_{13}$ | n-C$_6$H$_{13}$O | n-C$_6$H$_{13}$ |
| n-C$_4$H$_9$O | n-C$_7$H$_{15}$ | n-C$_5$H$_{11}$O | n-C$_7$H$_{15}$ | n-C$_6$H$_{13}$O | n-C$_7$H$_{15}$ |
| n-C$_4$H$_9$O | H | n-C$_5$H$_{11}$O | H | n-C$_6$H$_{13}$O | H |
| n-C$_4$H$_9$O | CH$_3$O | n-C$_5$H$_{11}$O | CH$_3$O | n-C$_6$H$_{13}$O | CH$_3$O |
| n-C$_4$H$_9$O | C$_2$H$_5$O | n-C$_5$H$_{11}$O | C$_2$H$_5$O | n-C$_6$H$_{13}$O | C$_2$H$_5$O |
| n-C$_4$H$_9$O | n-C$_3$H$_7$O | n-C$_5$H$_{11}$O | n-C$_3$H$_7$O | n-C$_6$H$_{13}$O | n-C$_3$H$_7$O |
| n-C$_4$H$_9$O | n-C$_4$H$_9$O | n-C$_5$H$_{11}$O | n-C$_4$H$_9$O | n-C$_6$H$_{13}$O | n-C$_4$H$_9$O |
| n-C$_4$H$_9$O | n-C$_5$H$_{11}$O | n-C$_5$H$_{11}$O | n-C$_5$H$_{11}$O | n-C$_6$H$_{13}$O | n-C$_5$H$_{11}$O |
| n-C$_4$H$_9$O | n-C$_6$H$_{13}$O | n-C$_5$H$_{11}$O | n-C$_6$H$_{13}$O | n-C$_6$H$_{13}$O | n-C$_6$H$_{13}$O |
| n-C$_4$H$_9$O | n-C$_7$H$_{15}$O | n-C$_5$H$_{11}$O | n-C$_7$H$_{15}$O | n-C$_6$H$_{13}$O | n-C$_7$H$_{15}$O |
| n-C$_4$H$_9$O | n-C$_8$H$_{17}$ | n-C$_5$H$_{11}$O | n-C$_8$H$_{17}$ | n-C$_6$H$_{13}$O | n-C$_8$H$_{17}$ |
| n-C$_4$H$_9$O | n-C$_8$H$_{17}$O | n-C$_5$H$_{11}$O | n-C$_8$H$_{17}$O | n-C$_6$H$_{13}$O | n-C$_8$H$_{17}$O |
| n-C$_4$H$_9$O | n-C$_9$H$_{19}$ | n-C$_5$H$_{11}$O | n-C$_9$H$_{19}$ | n-C$_6$H$_{13}$O | n-C$_9$H$_{19}$ |

TABLE 6-continued

Compounds of formula:

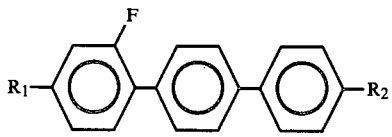

| | | | | | |
|---|---|---|---|---|---|
| n-C$_4$H$_9$O | n-C$_9$H$_{19}$O | n-C$_5$H$_{11}$O | n-C$_9$H$_{19}$O | n-C$_6$H$_{13}$O | n-C$_9$H$_{19}$ |
| n-C$_4$H$_9$O | n-C$_{10}$H$_{21}$ | n-C$_5$H$_{11}$O | n-C$_{10}$H$_{21}$ | n-C$_6$H$_{13}$O | n-C$_{10}$H$_{21}$ |
| n-C$_4$H$_9$O | n-C$_{10}$H$_{21}$O | n-C$_5$H$_{11}$O | n-C$_{10}$H$_{21}$O | n-C$_6$H$_{13}$O | n-C$_{10}$H$_{21}$O |
| n-C$_4$H$_9$O | n-C$_{11}$H$_{23}$ | n-C$_5$H$_{11}$O | n-C$_{11}$H$_{23}$ | n-C$_6$H$_{13}$O | n-C$_{11}$H$_{23}$ |
| n-C$_4$H$_9$O | n-C$_{12}$H$_{25}$ | n-C$_5$H$_{11}$O | n-C$_{12}$H$_{25}$ | n-C$_6$H$_{13}$O | n-C$_{12}$H$_{25}$ |
| n-C$_4$H$_9$O | n-C$_{12}$H$_{25}$O | n-C$_5$H$_{11}$O | n-C$_{12}$H$_{25}$O | n-C$_6$H$_{13}$O | n-C$_{12}$H$_{25}$O |

| R$_1$ | R$_2$ | R$_1$ | R$_2$ | R$_1$ | R$_2$ |
|---|---|---|---|---|---|
| n-C$_7$H$_{15}$O | CH$_3$ | n-C$_8$H$_{17}$O | CH$_3$ | n-C$_9$H$_{19}$O | CH$_3$ |
| n-C$_7$H$_{15}$O | C$_2$H$_5$ | n-C$_8$H$_{17}$O | C$_2$H$_5$ | n-C$_9$H$_{19}$O | C$_2$H$_5$ |
| n-C$_7$H$_{15}$O | n-C$_3$H$_7$ | n-C$_8$H$_{17}$O | n-C$_3$H$_7$ | n-C$_9$H$_{19}$O | n-C$_3$H$_7$ |
| n-C$_7$H$_{15}$O | n-C$_4$H$_9$ | n-C$_8$H$_{17}$O | n-C$_4$H$_9$ | n-C$_9$H$_{19}$O | n-C$_4$H$_9$ |
| n-C$_7$H$_{15}$O | n-C$_5$H$_{11}$ | n-C$_8$H$_{17}$O | n-C$_5$H$_{11}$ | n-C$_9$H$_{19}$O | n-C$_5$H$_{11}$ |
| n-C$_7$H$_{15}$O | n-C$_6$H$_{13}$ | n-C$_8$H$_{17}$O | n-C$_6$H$_{13}$ | n-C$_9$H$_{19}$O | n-C$_6$H$_{13}$ |
| n-C$_7$H$_{15}$O | n-C$_7$H$_{15}$ | n-C$_8$H$_{17}$O | n-C$_7$H$_{15}$ | n-C$_9$H$_{19}$O | n-C$_7$H$_{15}$ |
| n-C$_7$H$_{15}$O | H | n-C$_8$H$_{17}$O | n-C$_8$H$_{17}$ | n-C$_9$H$_{19}$O | n-C$_8$H$_{17}$ |
| n-C$_7$H$_{15}$O | CH$_3$O | n-C$_8$H$_{17}$O | CH$_3$O | n-C$_9$H$_{19}$O | H |
| n-C$_7$H$_{15}$O | C$_2$H$_5$O | n-C$_8$H$_{17}$O | C$_2$H$_5$O | n-C$_9$H$_{19}$O | CH$_3$O |
| n-C$_7$H$_{15}$O | n-C$_3$H$_7$O | n-C$_8$H$_{17}$O | n-C$_3$H$_7$O | n-C$_9$H$_{19}$O | C$_2$H$_5$O |
| n-C$_7$H$_{15}$O | n-C$_4$H$_9$O | n-C$_8$H$_{17}$O | n-C$_4$H$_9$O | n-C$_9$H$_{19}$O | n-C$_3$H$_7$O |
| n-C$_7$H$_{15}$O | n-C$_5$H$_{11}$O | n-C$_8$H$_{17}$O | n-C$_5$H$_{11}$O | n-C$_9$H$_{19}$O | n-C$_4$H$_9$O |
| n-C$_7$H$_{15}$O | n-C$_6$H$_{13}$O | n-C$_8$H$_{17}$O | n-C$_6$H$_{13}$O | n-C$_9$H$_{19}$O | n-C$_5$H$_{11}$O |
| n-C$_7$H$_{15}$O | n-C$_7$H$_{15}$O | n-C$_8$H$_{17}$O | n-C$_7$H$_{15}$O | n-C$_9$H$_{19}$O | n-C$_6$H$_{13}$O |
| n-C$_7$H$_{15}$O | n-C$_8$H$_{17}$ | n-C$_8$H$_{17}$O | n-C$_8$H$_{17}$O | n-C$_9$H$_{19}$O | n-C$_7$H$_{15}$O |
| n-C$_7$H$_{15}$O | n-C$_8$H$_{17}$O | n-C$_8$H$_{17}$O | n-C$_9$H$_{19}$ | n-C$_9$H$_{19}$O | n-C$_8$H$_{17}$O |
| n-C$_7$H$_{15}$O | n-C$_9$H$_{19}$ | n-C$_8$H$_{17}$O | n-C$_9$H$_{19}$O | n-C$_9$H$_{19}$O | n-C$_9$H$_{19}$ |
| n-C$_7$H$_{15}$O | n-C$_9$H$_{19}$O | n-C$_8$H$_{17}$O | n-C$_{10}$H$_{21}$ | n-C$_9$H$_{19}$O | n-C$_9$H$_{19}$O |
| n-C$_7$H$_{15}$O | n-C$_{10}$H$_{21}$ | n-C$_8$H$_{17}$O | n-C$_{10}$H$_{21}$O | n-C$_9$H$_{19}$O | n-C$_{10}$H$_{21}$ |
| n-C$_7$H$_{15}$O | n-C$_{10}$H$_{21}$O | n-C$_8$H$_{17}$O | n-C$_{11}$H$_{23}$ | n-C$_9$H$_{19}$O | n-C$_{10}$H$_{21}$O |
| n-C$_7$H$_{15}$O | n-C$_{11}$H$_{23}$ | n-C$_8$H$_{17}$O | n-C$_{12}$H$_{25}$ | n-C$_9$H$_{19}$O | n-C$_{11}$H$_{23}$ |
| n-C$_7$H$_{15}$O | n-C$_{12}$H$_{25}$ | n-C$_8$H$_{17}$O | n-C$_{12}$H$_{25}$O | n-C$_9$H$_{19}$O | n-C$_{12}$H$_{25}$O |
| n-C$_7$H$_{15}$O | n-C$_{12}$H$_{25}$O | | | | |
| n-C$_{10}$H$_{21}$O | CH$_3$ | n-C$_{11}$H$_{23}$O | CH$_3$ | n-C$_{12}$H$_{25}$O | CH$_3$ |
| n-C$_{10}$H$_{21}$O | C$_2$H$_5$ | n-C$_{11}$H$_{23}$O | C$_2$H$_5$ | n-C$_{12}$H$_{25}$O | C$_2$H$_5$ |
| n-C$_{10}$H$_{21}$O | n-C$_3$H$_7$ | n-C$_{11}$H$_{23}$O | n-C$_3$H$_7$ | n-C$_{12}$H$_{25}$O | n-C$_3$H$_7$ |
| n-C$_{10}$H$_{21}$O | n-C$_4$H$_9$ | n-C$_{11}$H$_{23}$O | n-C$_4$H$_9$ | n-C$_{12}$H$_{25}$O | n-C$_4$H$_9$ |
| n-C$_{10}$H$_{21}$O | n-C$_5$H$_{11}$ | n-C$_{11}$H$_{23}$O | n-C$_5$H$_{11}$ | n-C$_{12}$H$_{25}$O | n-C$_5$H$_{11}$ |
| n-C$_{10}$H$_{21}$O | n-C$_6$H$_{13}$ | n-C$_{11}$H$_{23}$O | n-C$_6$H$_{13}$ | n-C$_{12}$H$_{25}$O | n-C$_6$H$_{13}$ |
| n-C$_{10}$H$_{21}$O | n-C$_7$H$_{15}$ | n-C$_{11}$H$_{23}$O | n-C$_7$H$_{15}$ | n-C$_{12}$H$_{25}$O | n-C$_7$H$_{15}$ |
| n-C$_{10}$H$_{21}$O | n-C$_8$H$_{17}$ | n-C$_{11}$H$_{23}$O | n-C$_8$H$_{17}$ | n-C$_{12}$H$_{25}$O | n-C$_8$H$_{17}$ |
| n-C$_{10}$H$_{21}$O | n-C$_9$H$_{19}$ | n-C$_{11}$H$_{23}$O | n-C$_9$H$_{19}$ | n-C$_{12}$H$_{25}$O | n-C$_9$H$_{19}$ |
| n-C$_{10}$H$_{21}$O | n-C$_{10}$H$_{21}$ | n-C$_{11}$H$_{23}$O | n-C$_{10}$H$_{21}$ | n-C$_{12}$H$_{25}$O | n-C$_{10}$H$_{21}$ |
| n-C$_{10}$H$_{21}$O | n-C$_{11}$H$_{23}$ | n-C$_{11}$H$_{23}$O | n-C$_{11}$H$_{23}$ | n-C$_{12}$H$_{25}$O | n-C$_{11}$H$_{23}$ |
| n-C$_{10}$H$_{21}$O | n-C$_{12}$H$_{25}$ | n-C$_{11}$H$_{23}$O | n-C$_{12}$H$_{25}$ | n-C$_{12}$H$_{25}$O | n-C$_{12}$H$_{25}$ |
| n-C$_{10}$H$_{21}$O | H | n-C$_{11}$H$_{23}$O | H | n-C$_{12}$H$_{25}$O | H |
| n-C$_{10}$H$_{21}$O | CH$_3$O | n-C$_{11}$H$_{23}$O | CH$_3$O | n-C$_{12}$H$_{25}$O | CH$_3$O |
| n-C$_{10}$H$_{21}$O | C$_2$H$_5$O | n-C$_{11}$H$_{23}$O | C$_2$H$_5$O | n-C$_{12}$H$_{25}$O | C$_2$H$_5$O |
| n-C$_{10}$H$_{21}$O | n-C$_3$H$_7$O | n-C$_{11}$H$_{23}$O | n-C$_3$H$_7$O | n-C$_{12}$H$_{25}$O | n-C$_3$H$_7$O |
| n-C$_{10}$H$_{21}$O | n-C$_4$H$_9$O | n-C$_{11}$H$_{23}$O | n-C$_4$H$_9$O | n-C$_{12}$H$_{25}$O | n-C$_4$H$_9$O |
| n-C$_{10}$H$_{21}$O | n-C$_5$H$_{11}$O | n-C$_{11}$H$_{23}$O | n-C$_5$H$_{11}$O | n-C$_{12}$H$_{25}$O | n-C$_5$H$_{11}$O |
| n-C$_{10}$H$_{21}$O | n-C$_6$H$_{13}$O | n-C$_{11}$H$_{23}$O | n-C$_6$H$_{13}$O | n-C$_{12}$H$_{25}$O | n-C$_6$H$_{13}$O |
| n-C$_{10}$H$_{21}$O | n-C$_7$H$_{15}$O | n-C$_{11}$H$_{23}$O | n-C$_7$H$_{15}$O | n-C$_{12}$H$_{25}$O | n-C$_7$H$_{15}$O |
| n-C$_{10}$H$_{21}$O | n-C$_8$H$_{17}$O | n-C$_{11}$H$_{23}$O | n-C$_8$H$_{17}$O | n-C$_{12}$H$_{25}$O | n-C$_8$H$_{17}$O |
| n-C$_{10}$H$_{21}$O | n-C$_9$H$_{19}$O | n-C$_{11}$H$_{23}$O | n-C$_{19}$H$_{19}$O | n-C$_{12}$H$_{25}$O | n-C$_9$H$_{19}$O |
| n-C$_{10}$H$_{21}$O | n-C$_{10}$H$_{21}$O | n-C$_{11}$H$_{23}$O | n-C$_{10}$H$_{21}$O | n-C$_{12}$H$_{25}$O | n-C$_{10}$H$_{21}$O |
| n-C$_{10}$H$_{21}$O | n-C$_{12}$H$_{25}$O | n-C$_{12}$H$_{23}$O | n-C$_{12}$H$_{25}$O | n-C$_{12}$H$_{25}$O | n-C$_{12}$H$_{25}$O |

The superiority of the fluorinated compounds of Formula I compared with known analogues containing no fluorine which are of Formula A given above is illustrated in Table 7 as follows.

TABLE 7

Properties of compounds of formula:

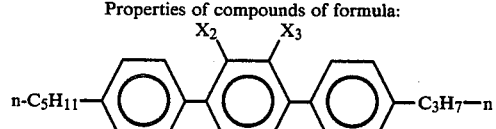

(a) Compounds characterised by groups X$_2$ and X$_3$

| Compound No. | X$_2$ | X$_3$ | Generalised Formula |
|---|---|---|---|
| PA1 | H | H | A |
| 9 | F | H | I |

TABLE 7-continued

Properties of compounds of formula:

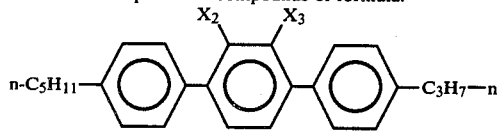

| | | | |
|---|---|---|---|
| 19 | H | F | I |

(b) Transition temperatures of Compound Nos 1 to 3:

| Compound No. | C-$S_E$ | C-$S_A$ | C-N | $S_E$-$S_B$ | $S_B$-I | $S_A$-N | N-I |
|---|---|---|---|---|---|---|---|
| PA1 | 174 | — | — | 200.7 | 217.7 | — | — |
| 9 | — | — | 50 | — | — | — | 140.6 |
| 19 | — | 61 | — | — | — | 99.5 | 141.5 |

As seen from Table 7 the known Compound No PA1 has a high melting point, a narrow liquid crystalline temperature range and no nematic liquid crystalline phase. Its liquid crystalline phases are entirely smectic in nature.

In contrast, Compound Nos 9 and 19 embodying the invention have a considerably lower melting point, a wide liquid crystalline temperature range in which the smectic region is suppressed or eliminated, but in any even is considerably lowered in temperature, and the nematic region is considerably enhanced.

The improvements illustrated in Table 7 in the properties of the Compounds Nos 9 and 19 per se lead also to corresponding improvements in the properties of mixtures in which the Compounds Nos 9 and 19 are incorporated, eg reduced viscosity, and reduced tendency to form injected smectic phases, as compared with corresponding mixtures containing Compound No PA1.

In fact, incorporation of fluorine in the basic terphenyl molecule of Compound No PA1 to form Compound Nos 9 and 19 effectively converts the structure from one having little practical use to one which is highly attractive for use in commercial devices.

Examples of the main transition temperatures of various alkoxy-terminated compounds of Formula I are as given in Table A1 as follows:

TABLE A1

Compounds of formula:

$$n\text{-}R_1 - \bigcirc - \bigcirc(F) - \bigcirc - R_2\text{-}n$$

| Compound Number | $R_1$ | $R_2$ | Melting point (°C.) | N-I (°C.) |
|---|---|---|---|---|
| 22 | $CH_3O$ | $C_5H_{11}$ | 60.5 | 117.5 |
| 23 | $C_2H_5O$ | $C_5H_{11}$ | 88.0 | 186.0 |
| 24 | $C_4H_9O$ | $C_3H_7$ | 92.0 | 180.0 |
| 25 | $C_4H_9O$ | $C_5H_{11}$ | 65.5 | 172.5 |
| 26 | $C_3H_7$ | $C_4H_9O$ | 103.0 | 183.0 |
| 27 | $C_5H_{11}$ | $C_2H_5O$ | 98.0 | 191.5 |
| 28 | $C_5H_{11}$ | $C_4H_9O$ | 59.5 | 176.0 |
| 29 | $C_8H_{17}$ | $C_2H_5O$ | 107.0 | 170.5 |
| 30 | $C_9H_{19}$ | $C_2H_5O$ | 92.0 | 167.5 |
| 31 | $CH_3O$ | $C_2H_5O$ | 165.0 | 244.3 |
| 32 | $C_2H_5O$ | $C_4H_9O$ | 140.0 | 225.6 |
| 33 | $C_4H_9O$ | $C_2H_5O$ | 136.0 | 226.0 |
| 34 | $C_4H_9O$ | $C_4H_9O$ | 139.0 | 222.5 |
| 35 | $C_7H_{15}O$ | $C_2H_5O$ | 125.0 | 201.5 |

Examples of other transition temperatures of various compounds listed in Table A1 are given in Table A2 as follows:

TABLE A2

| Compound Number | Transition Temperatures (°C.) | | | | | |
|---|---|---|---|---|---|---|
| | C—C | $S_E$-$S_B$ | $S_B$-$S_C$ | $S,S_C$-$S_A$ | $S_C$-N | $S_A$-N |
| 25 | | | | | | 96.5 |
| 26 | 78.0 | | | 112.5 | | 135.0 |
| 28 | | 85.5 | 86.5 | 99.5 | | 144.0 |
| 33 | 136.0 | | | | | |
| 34 | 118.0 | | | | 144.5 | |

Figure 12:
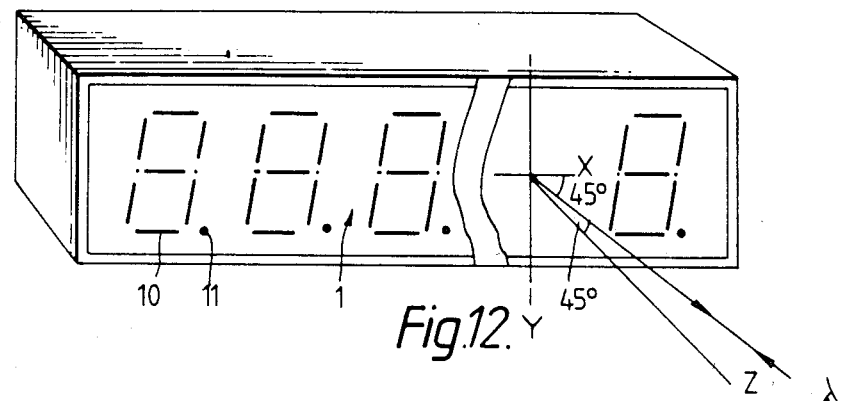
FIGS. 12 to 18 are illustrations of examples of liquid crystal devices incorporating liquid crystal materials containing compounds of Formula I; these Figures are further described below.

Examples of electro-optical devices embodying the invention will now be described by way of example only with reference to the following drawings wherein:

FIG. 11 is a sectional view of a twisted nematic digital display:

FIG. 12 is a sectional view of the display shown in FIG. 11.

Figure 13:
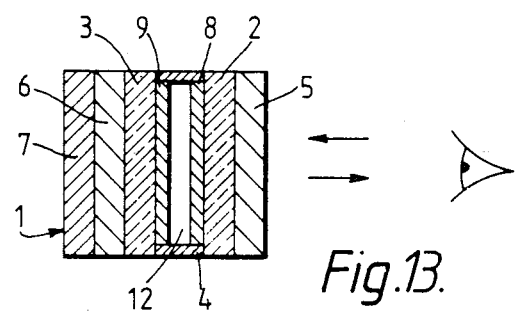
Figure 14:
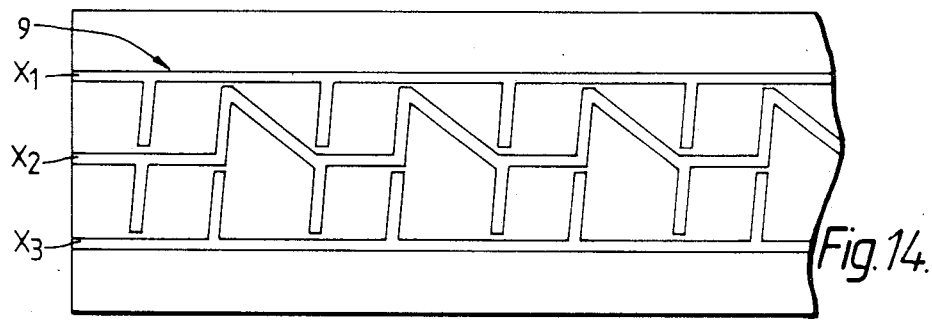
Figure 15:
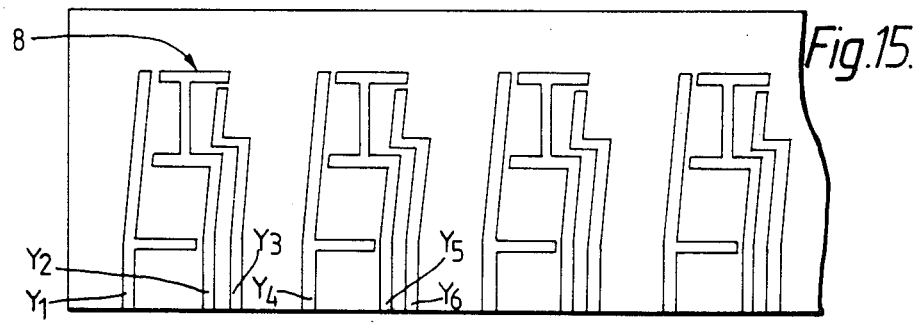
Figure 16:
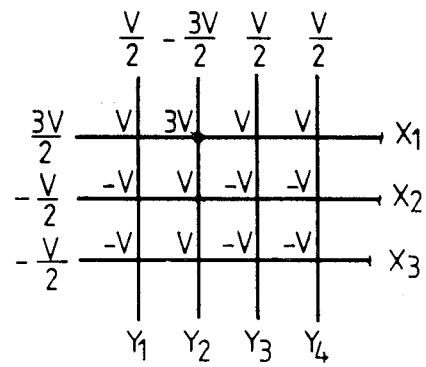
Figure 17:
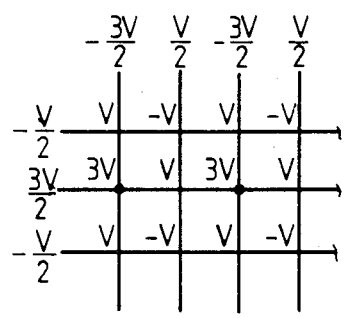

FIG. 13 shows a rear electrode configuration for FIG. 1;

FIG. 14 shows a front electrode configuration for FIG. 1;

FIGS. 15, 16 and 17 show schematic views of the device of FIGS. 11 to 14 with typical addressing voltages.

Examples of electro-optical devices embodying the invention will now be described by way of example only with reference to the following drawings wherein:

FIG. 12 is a sectional view of a twisted nematic digital display;

FIG. 13 is a sectional view of the display shown in FIG. 12.

Figure 18:
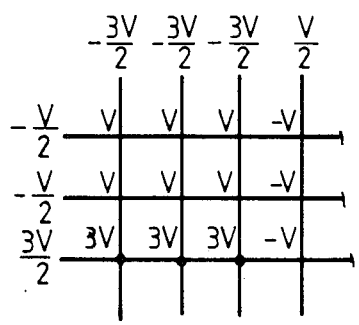

FIG. 14 shows a rear electrode configuration for FIG. 1;

FIG. 14 shows a front electrode configuration of FIG. 1;

FIGS. 16, 17 and 18 show schematic views of the device of FIGS. 12 to 15 with typical addressing voltages.

The display of FIGS. 11 to 14 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 13 the rear electrode structure is formed into three electrodes $x_1, x_2, x_3$. Similarly the front electrode structure is formed into three electrodes per digit and decimal point $y_1, y_2, y_3$ .... Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surface lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 11 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2,3, ie along the axis Z. Thus light at the position does not reach the reflector 7 and does not reflect back to the observer who sees a dark display of one or more bars of a digit 10.

Voltages are applied as follows as shown in FIGS. 15, 16 and 17 for three successive time intervals in a linescan fashion. An electrical potential of 3 V/2 is applied to, ie scanned down, each x electrode in turn whilst −V/2 is applied to the remaining x electrodes. Meanwhile −3 V/2 or V/2 is applied to the y electrodes. A coincidence or 3 V/2 and −3 V/2 at an intersection results in a voltabe 3 V across the liquid crystal layer 12. Elsewhere the voltage is V or −V. Thus by applying −3 V/2 to appropriate y electrodes as 3 V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 12 to 18 is a multiplexed display because the electrodes are shared between ON and OFF intersections or display elements.

A material embodying the invention which is suitable for use as the material 12 in the above device is in Table as follows (Mixture 1).

TABLE 8

| Mixture 1 | Weight Percentage |
|---|---|

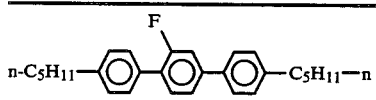

20

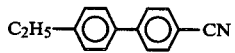

10

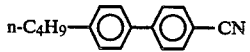

10

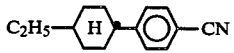

10

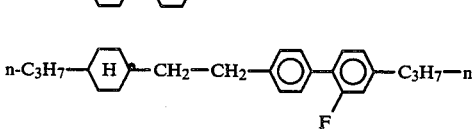

10

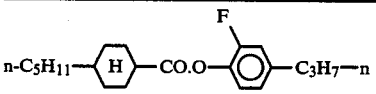

20

TABLE 8-continued

| Mixture 1 | Weight Percentage |
|---|---|

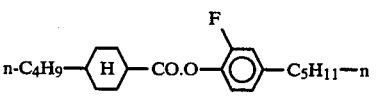

20

Small amounts of an optically active material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable optically active materials are:

C15: about 0.1–0.5% by weight and CB15: and 0.01% to 0.05% by weight.

C15 is (+)-CH$_3$.CH$_2$.CH.CH$_2$- 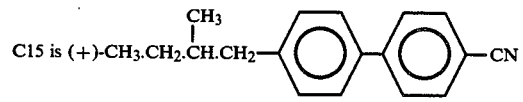 -CN

CB15 is (+)-CH$_3$.CH$_2$.CH.CH$_2$- 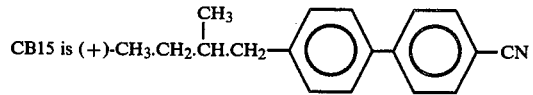 -CN

Small amounts of pleochroic dye may be added to enhance the display contrast, eg 2% by weight of dye Mixture 2 specified in UK Patent Specification No. 2093475A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (hemotropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Fréedericksz effect cell made in the above way may incorporate Mixture 3 below, the cell specing being 10 μm.

TABLE 9

| Mixture 3 | |
|---|---|
| Compound | Weight Percentage |

30

30

TABLE 9-continued

Mixture 3

| Compound | Weight Percentage |
|---|---|
| n-C$_5$H$_{11}$—(H)—CH$_2$.CH$_2$—⌬—⌬(F)—C$_2$H$_5$ | 20 |
| n-C$_5$H$_{11}$—⌬—⌬(F)—⌬—C$_3$H$_7$-n | 20 |

Compound A =

C$_2$H$_5$—(H)—CO.O—⌬(CN)(CN)—O.OC—(H)—C$_2$H$_5$ may optionally be added to Mixture 3 (up to 3% by weight of Mixture 3) as a negative additive.

The preparation of Compound A is described in published UK Patent Application No 2061256A. About 1% by weight of a the dye mixture specified above may be added to Mixture 3 to give a dyed mixture. (Mixture 3A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, eg treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular configuration in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, eg with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides, the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (eg 1% by weight of the dye mixture specified above in the case where $\Delta\epsilon$ is positive) to the liquid crystal material.

A suitable positive dielectric anisotropy material, Mixture 4, embodying the invention for use in a phase change effect (negative contrast type) device is:

TABLE 10

Mixture 4

| Compound | | Weight Percentage |
|---|---|---|
| Mixture B { C$_6$H$_{13}$—⌬—⌬—CN 37.5% | | |
| n-C$_4$H$_9$—⌬—⌬—CN 37.5% | | 30 |
| n-C$_3$H$_7$O—⌬—⌬—CN 25% } | | |
| n-C$_5$H$_{11}$—(H)—CH$_2$.CH$_2$—⌬—⌬(F)—C$_2$H$_5$ | | 23 |
| CB15 = R$_c$—⌬—⌬—CN | | 4 |
| (R$_c$ = (+)-2-methylbutyl) | | |
| n-C$_5$H$_{11}$—⌬—⌬(F)—⌬—C$_3$H$_7$-n | | 23 |
| n-C$_5$H$_{11}$—⌬—⌬(F)—⌬—C$_5$H$_{11}$-n | | 20 |

A suitable negative dielectric anisotropy material embodying the invention for use in a phase change effect (positive contrast type) device, Mixture 5, is as follows:

TABLE 11

Mixture 5

| Material | Weight Percentage |
|---|---|
| Mixture 3 | 99 |
| R$_c$—⌬—⌬—CO.O—⌬—R$_c$ | 1 |

(R$_c$ = (+)-2-methylbutyl)

As an alternative to the chiral compound specified in Table 11 a chiral compound of Formula I may be used.

We claim:
1. A terphenyl having a formula:

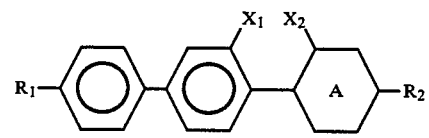

wherein:
R$_1$ is selected from H, alkyl, alkoxy, alkylcarbonyl, alkylcarbonyloxy and alkoxycarbonyloxy;
R$_2$ is selected from H, alkyl, alkoxy;
X$_1$ is selected from H and fluorine;
X$_2$ is selected from H and fluorine;
and is selected from

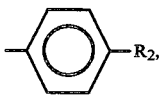

and

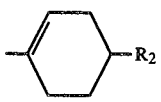

provided that one of $X_1$ and $X_2$ is fluorine.

2. A terphenyl as claimed in claim 1 and wherein

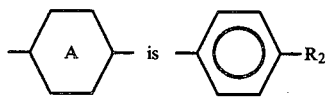

3. A terphenyl as claimed in claim 2 and wherein $R_1$ is H, alkyl or alkoxy provided that at least one of $R_1$ and $R_2$ is alkyl alkoxy.

4. A terphenyl as claimed in claim 3 and wherein $X_1$ is hydrogen and $X_2$ is fluorine.

5. A terphenyl as claimed in claim 4 and wherein $R_1$ is n-alkyl or n-alkoxy having from 1 to 12 carbon atoms and $R_2$ is n-alkyl or n-alkoxy having from 1 to 12 carbon atoms.

* * * * *